United States Patent
Fujii et al.

(10) Patent No.: US 10,342,500 B2
(45) Date of Patent: Jul. 9, 2019

(54) X-RAY CT APPARATUS, UPSAMPLING METHOD OF PROJECTION DATA, AND IMAGE RECONSTRUCTION METHOD

(71) Applicant: HITACHI, LTD., Tokyo (JP)

(72) Inventors: Hideaki Fujii, Tokyo (JP); Taiga Goto, Tokyo (JP); Tetsuo Nakazawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 335 days.

(21) Appl. No.: 15/518,933

(22) PCT Filed: Nov. 13, 2015

(86) PCT No.: PCT/JP2015/081995
§ 371 (c)(1),
(2) Date: Apr. 13, 2017

(87) PCT Pub. No.: WO2016/080311
PCT Pub. Date: May 26, 2016

(65) Prior Publication Data
US 2017/0231589 A1     Aug. 17, 2017

(30) Foreign Application Priority Data
Nov. 21, 2014  (JP) ................. 2014-236240

(51) Int. Cl.
*H05G 1/00*     (2006.01)
*A61B 6/00*     (2006.01)
(Continued)

(52) U.S. Cl.
CPC ............ *A61B 6/5205* (2013.01); *A61B 6/032* (2013.01); *A61B 6/0457* (2013.01);
(Continued)

(58) Field of Classification Search
CPC ..... A61B 6/4452; A61B 6/032; A61B 6/0457; A61B 6/52
See application file for complete search history.

(56) References Cited

U.S. PATENT DOCUMENTS

2006/0018439 A1\* 1/2006 Tang .................. A61B 6/032
378/210

FOREIGN PATENT DOCUMENTS

| JP | 2007-97754 | 4/2007 |
| JP | 2010-104480 | 5/2010 |
| JP | 2015-33442 | 2/2015 |

OTHER PUBLICATIONS

International Search Report dated Dec. 28, 2015 in connection with PCT/JP2015/081995.

\* cited by examiner

*Primary Examiner* — Don K Wong
(74) *Attorney, Agent, or Firm* — Cooper & Dunham LLP

(57) ABSTRACT

In a case where helical scanning, etc., is performed in an X-ray CT apparatus, upsampled projection data that more approximates to an observed value is obtained. There is provided an X-ray CT apparatus that improves spatial resolution of an overall effective field of view without reducing rotation speed, in an FFS method of acquiring projection data through moving of an X-ray focus position to a plurality of positions. The X-ray CT apparatus: converts projection data acquired through helical scanning into projection data of normal scanning performed by one rotation; generates a virtual-counter-data space in which virtual counter data are acquired on substantially coincident X-ray transmission path in the converted projection data; performs upsampling in a view direction; and similarly upsamples FFS projection data in the view direction for focus-shifted projection data obtained by performing the helical scanning while causing (Continued)

the X-ray focus position to shift (virtual counter data space generation).

18 Claims, 33 Drawing Sheets

(51) Int. Cl.
*A61B 6/03* (2006.01)
*A61B 6/04* (2006.01)
(52) U.S. Cl.
CPC ............ *A61B 6/4452* (2013.01); *A61B 6/461* (2013.01); *A61B 6/469* (2013.01)

FIG.4
(a) 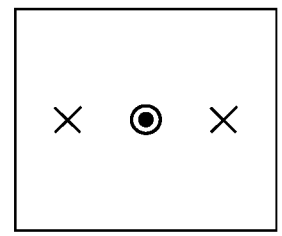
(b) 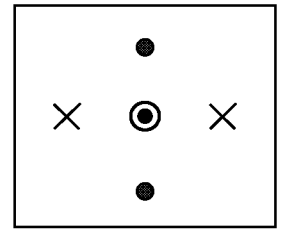
(c) 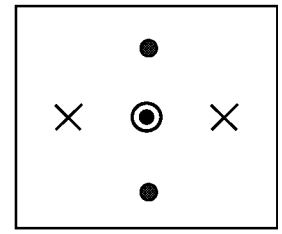

FIG.8
(a)
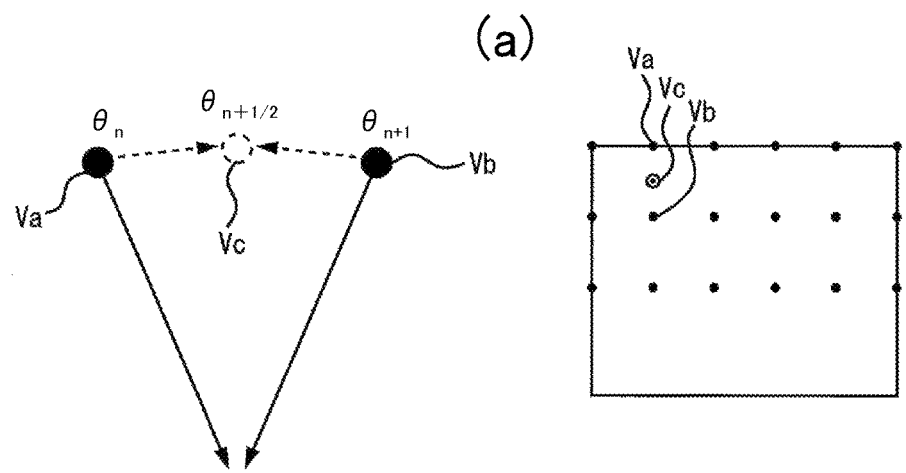
(b)
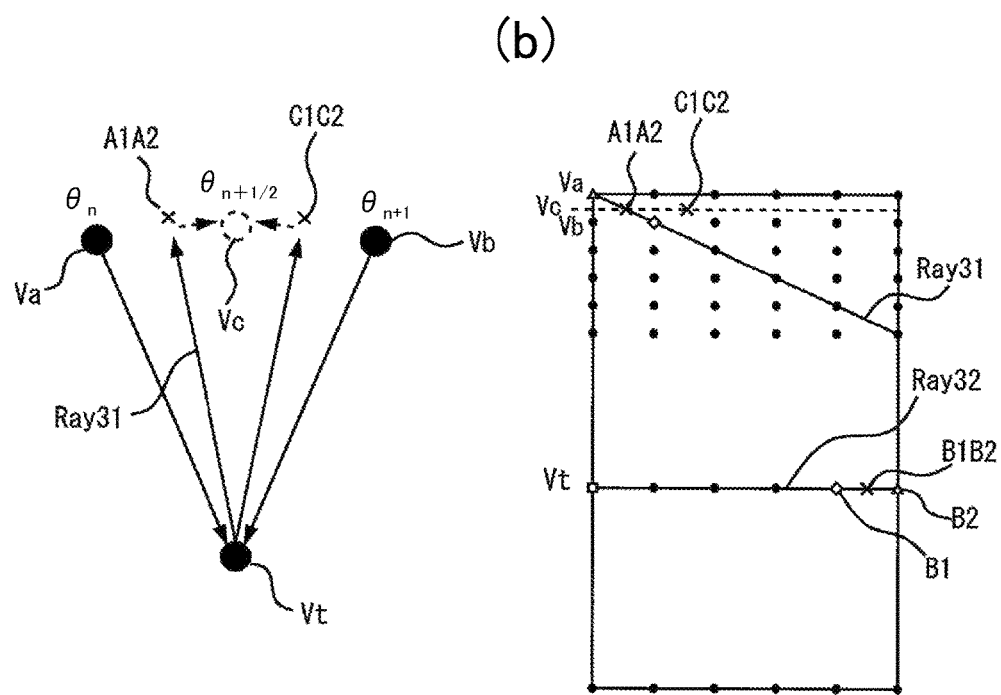

FIG.20
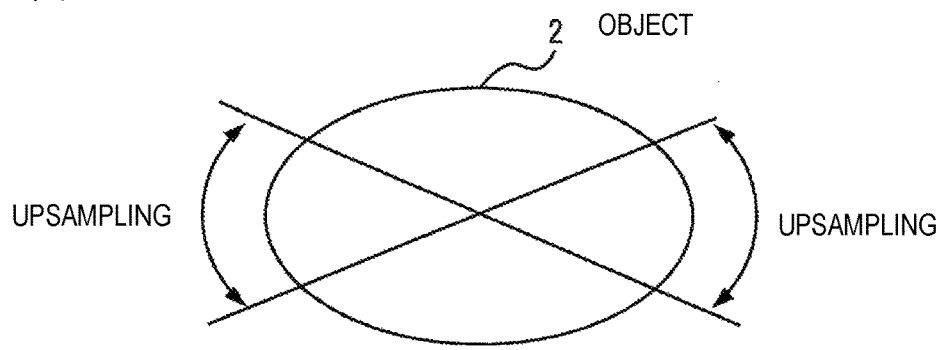
(a)
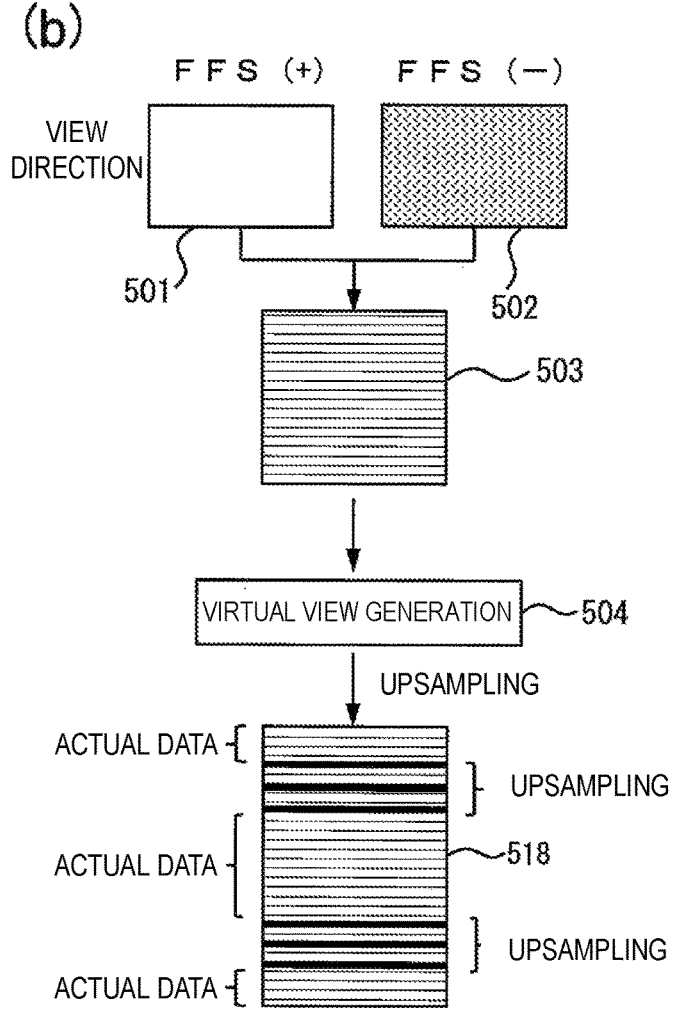
(b)

FIG.21
(a) 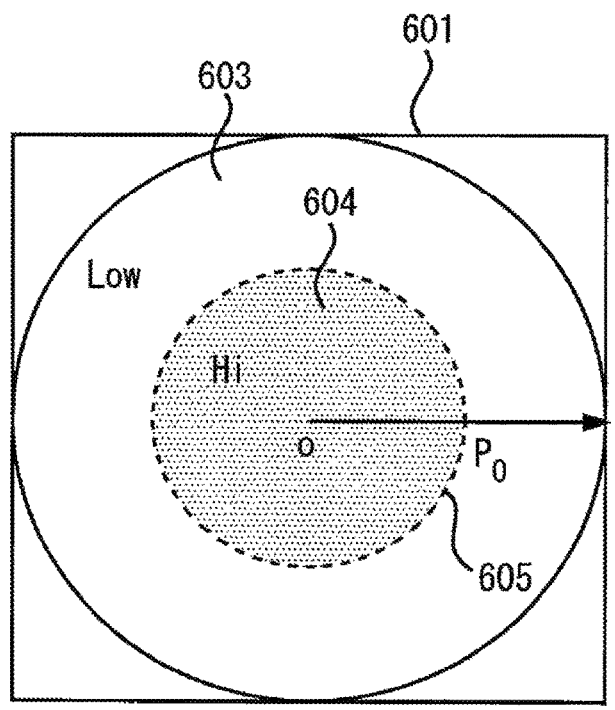
(b) 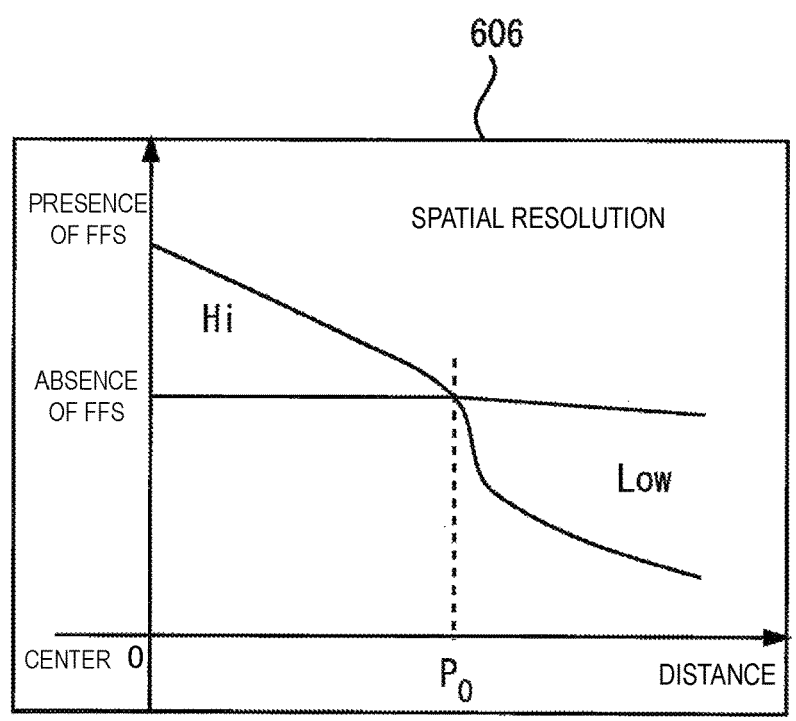

FIG.23
(a) 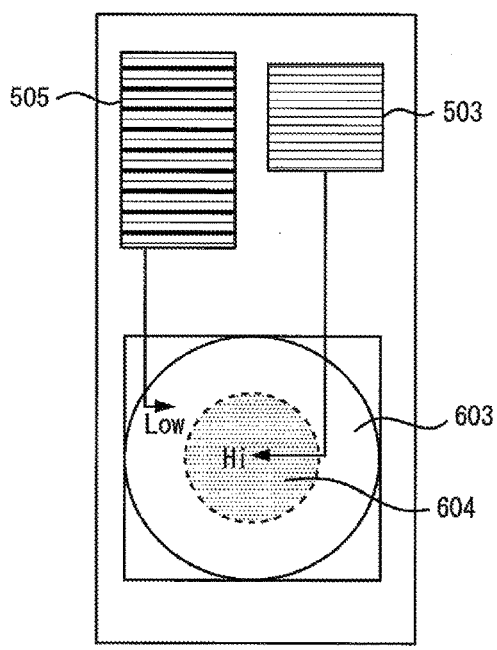
(b) 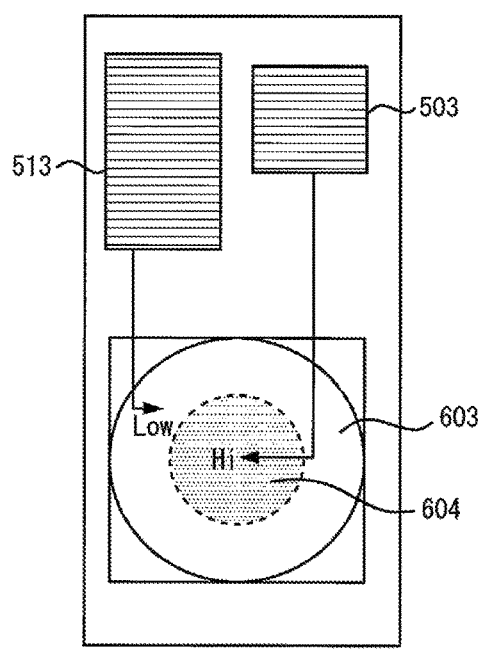
(c) 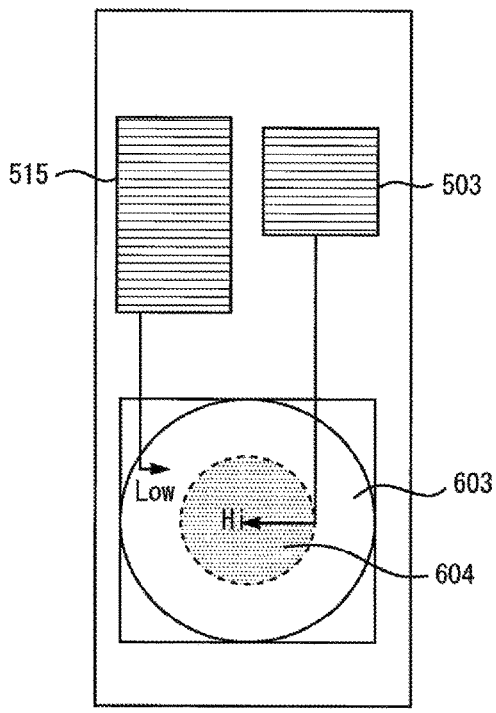
(d) 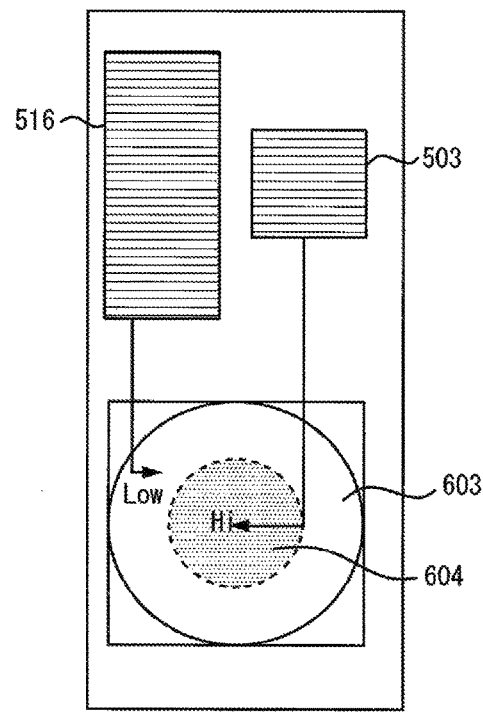

FIG.24
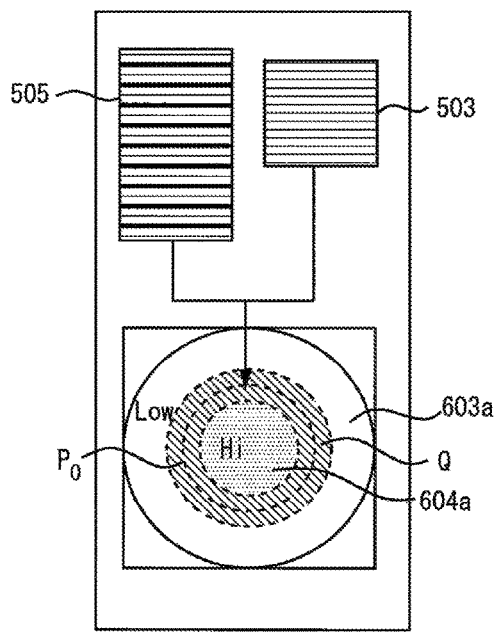
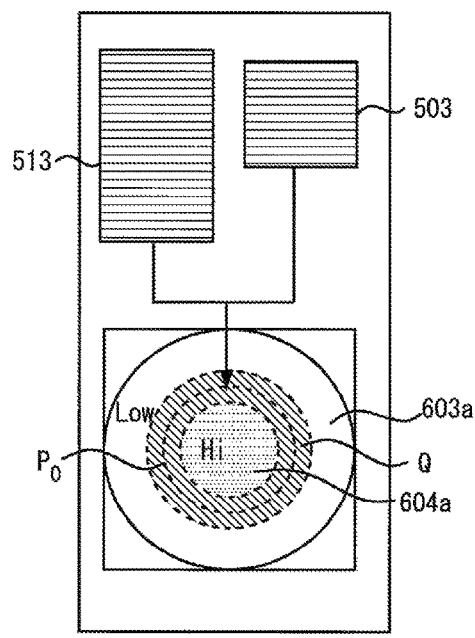
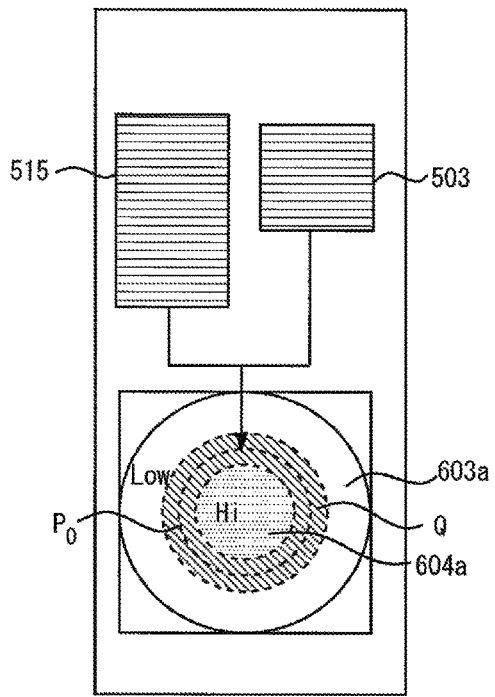
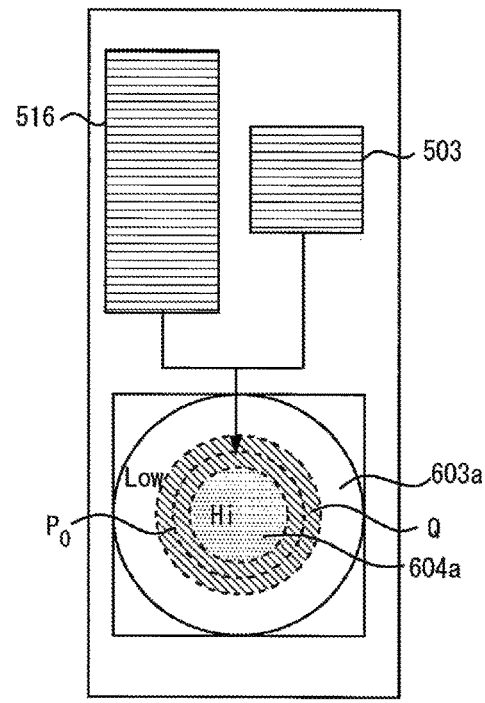

FIG.29
(a) 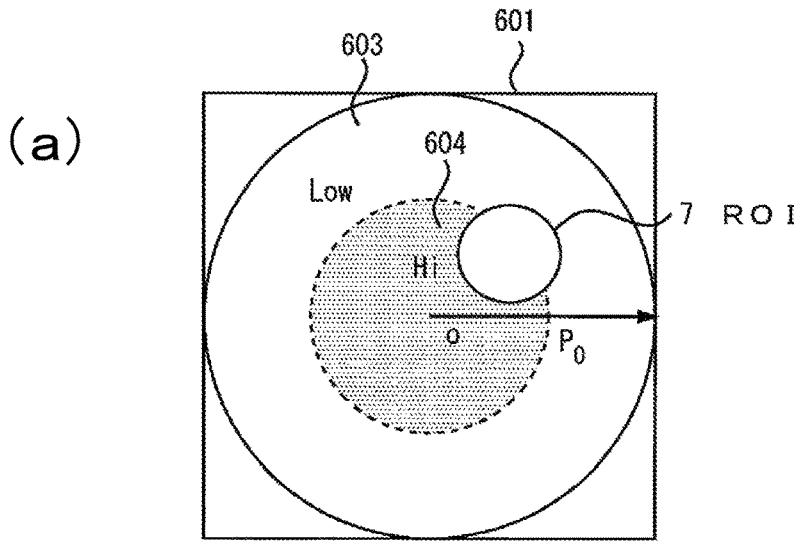
(b) 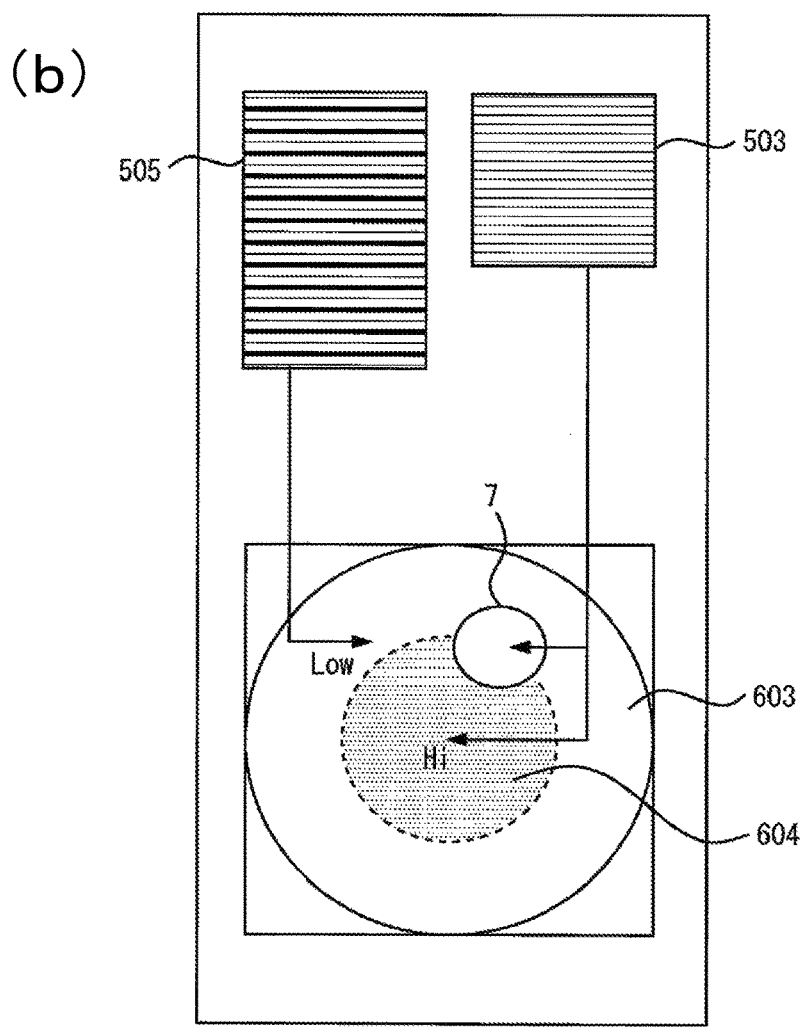

X-RAY CT APPARATUS, UPSAMPLING METHOD OF PROJECTION DATA, AND IMAGE RECONSTRUCTION METHOD

TECHNICAL FIELD

The present invention relates to an X-ray CT apparatus, an upsampling method of projection data, and an image reconstruction method, specifically, to generation of upsampled projection data for increasing, through calculation, the number of views, the number of channels, or the number of rows of object projection data of measurement through helical scanning, continuous reciprocating scanning, or the like, and to the image reconstruction method using the upsampled projection data.

BACKGROUND ART

An X-ray CT apparatus causes an X-ray tube device (X-ray source) and an X-ray detector to revolve around an object with the X-ray tube device and the X-ray detector disposed to face each other, performs irradiation with X-rays in a plurality of rotation angle directions (views), then detects X-rays transmitted through the object for each view, and generates a tomogram of the object, based on detected projection data. In such an X-ray CT apparatus, the X-ray tube device and the X-ray detector are caused to revolve and a couch and a scanner gantry are caused to relatively move in a body-axial direction, and thereby helical scanning, in which scanning is performed in a spiral manner, is performed. In addition, in the X-ray CT apparatus, in order to improve spatial resolution of an image, for example a method of scanning by increasing the number of views per 360-degree rotation has been proposed.

However, a sampling rate or the like of the data collecting device is likely to be limited due to hardware limit or the like.

PTL 1 discloses a method of increasing, through calculation, the number of views of acquired projection data. In a technology of PTL 1, the projection data is interpolated within a selected view range and an interpolation view is generated. In general, the interpolation means that a value of a point as a target is obtained by using values of a plurality of points around the point as the target.

CITATION LIST

Patent Literature

PTL 1: JP-A-2001-286462

SUMMARY OF INVENTION

Technical Problem

However, in the X-ray CT apparatus, a difference in view causes data of passing through a different X-ray transmission path to be acquired. Hence, in a case where adjacent views have a large interval, information different from actual information of an object is likely to be contained when a value of an interpolation view is obtained by using only values of the two adjacent views. Hence, when an image is reconstructed, by using projection data upsampled in the technology of PTL 1, created information is likely to be contained in the image, and thus a clinical problem arises.

In consideration of the problem described above, an object of the present invention is to provide an X-ray CT apparatus or the like that is capable of acquiring upsampled projection data that more approximates to an observed value in a case where helical scanning or the like is performed.

Solution to Problem

In order to achieve the object described above, according to the present invention, there is provided an X-ray CT apparatus including: an X-ray tube device that performs irradiation with X-rays; an X-ray detector that is disposed to face the X-ray tube device and detects transmitted X-rays as X-rays transmitted through an object; a rotary disk on which the X-ray tube device and the X-ray detector are mounted and which rotates around the object; a scanner gantry on which the rotary disk is mounted; a couch on which the object is positioned; a scanning control unit that causes the couch and the scanner gantry to relatively move in a body-axial direction while causing the rotary disk to rotate and collects data of the transmitted X-rays detected by the X-ray detector; a projection-data converting unit that performs predetermined data processing on the collected data of transmitted X-rays and generates projection data required for reconstruction of a tomogram at a target slice position; an upsampled-projection-data generating unit that generates virtual counter data containing counter data acquired on substantially coincident X-ray transmission path in the projection data, thereby upsampling the projection data; a reconstruction calculating unit that reconstructs an image by using upsampled projection data as projection data subjected to upsampling; and a display unit that displays an image reconstructed by the reconstruction calculating unit.

In addition, according to the present invention, there is provided an X-ray CT apparatus including: an X-ray tube device that performs irradiation with X-rays from a plurality of focus positions; an X-ray detector that is disposed to face the X-ray tube device and detects transmitted X-rays as X-rays transmitted through an object; a rotary disk on which the X-ray tube device and the X-ray detector are mounted and which rotates around the object; a scanner gantry on which the rotary disk is mounted; a couch on which the object is positioned; a focus-shifted-scanning control unit that causes the couch and the scanner gantry to relatively move in a body-axial direction while causing the rotary disk to rotate and collects data of the transmitted X-rays from the X-rays with which irradiation is performed by causing the focus position to shift to any positions; a projection-data converting unit that performs predetermined data processing on the collected data of transmitted X-rays from the focus positions and generates projection data required for reconstruction of a tomogram at a target slice position; an upsampled-projection-data generating unit that generates virtual counter data containing counter data acquired on substantially coincident X-ray transmission path in the projection data, generates a virtual view in a view direction, and combines items of projection data of focus positions in which the virtual view is inserted, thereby generating upsampled projection data; a reconstruction calculating unit that reconstructs an image by using the upsampled projection data; and a display unit that displays an image reconstructed by the reconstruction calculating unit.

In addition, according to the present invention, there is provided an upsampling method of projection data that is executed by an image calculating device, the method including: a step of collecting data of object-transmitted X-rays measured by scanning of causing a couch and a scanner gantry to relatively move in a body-axial direction while causing a rotary disk of an X-ray CT apparatus to rotate; a step of performing predetermined data processing on the collected data of object-transmitted X-rays and generating projection data required for reconstruction of a tomogram at a target slice position; and a step of generating virtual counter data containing counter data acquired on substantially coincident X-ray transmission path in the projection data, and upsampling the projection data.

In addition, according to the present invention, there is provided an image reconstruction method including: a step of causing a couch and a scanner gantry to relatively move in a body-axial direction while causing a rotary disk to rotate and collecting data of transmitted X-rays from the X-rays with which irradiation is performed by causing an X-ray focus position to shift to a plurality of positions in an X-ray tube device; a step of performing predetermined data processing on the collected data of transmitted X-rays from the focus positions and generating projection data required for reconstruction of a tomogram at a target slice position; a step of generating virtual counter data containing counter data acquired on substantially coincident X-ray transmission path in the projection data, generating a virtual view in a view direction, combining items of projection data of focus positions in which the virtual view is inserted, and generating upsampled projection data; a step of generating focus-shifted projection data acquired by combining items of the projection data at the focus positions without the virtual view inserted; and a step of reconstructing an image by using the focus-shifted projection data in a central region close to the center of the image from a predetermined boundary in an image plane and by using the upsampled projection data in a peripheral region on an outer side from the boundary.

Advantageous Effects of Invention

According to the present invention, it is possible to provide the X-ray CT apparatus that is capable of obtaining the upsampled projection data that more approximates to an observed value in a case where helical scanning or the like is performed.

BRIEF DESCRIPTION OF DRAWINGS

FIG. 4(a) illustrates a diagram of interpolation using two points, FIG. 4(b) illustrates a diagram of interpolation using four points, and FIG. 4(c) illustrates a diagram of interpolation using a TV method.

FIG. 8 illustrates diagrams for showing a difference between upsampling in simple view interpolation in FIG. 8(a) and upsampling according to the present invention in FIG. 8(b).

FIG. 20 illustrates diagrams of upsampled projection data 518 that is partially different in the number of views.

FIG. 21 illustrates diagrams for showing a change in spatial resolution in a central region 604 and a peripheral region 603 of an image.

FIG. 23 illustrates diagrams of aspects of projection data that is used in the reconstruction calculating process in FIG. 22.

FIG. 24 illustrates diagrams for showing a reconstruction calculating process of a third embodiment.

FIG. 29 illustrates conceptual diagrams for showing an ROI that is set in a reconstruction calculating process and projection data that is used in regions of a fifth embodiment.

DESCRIPTION OF EMBODIMENTS

Hereinafter, a preferred embodiment according to the present invention will be described in detail with reference to the accompanying figures.

First Embodiment

First, an entire configuration of an X-ray CT apparatus 1 is described with reference to FIG. 1.

Figure 1:
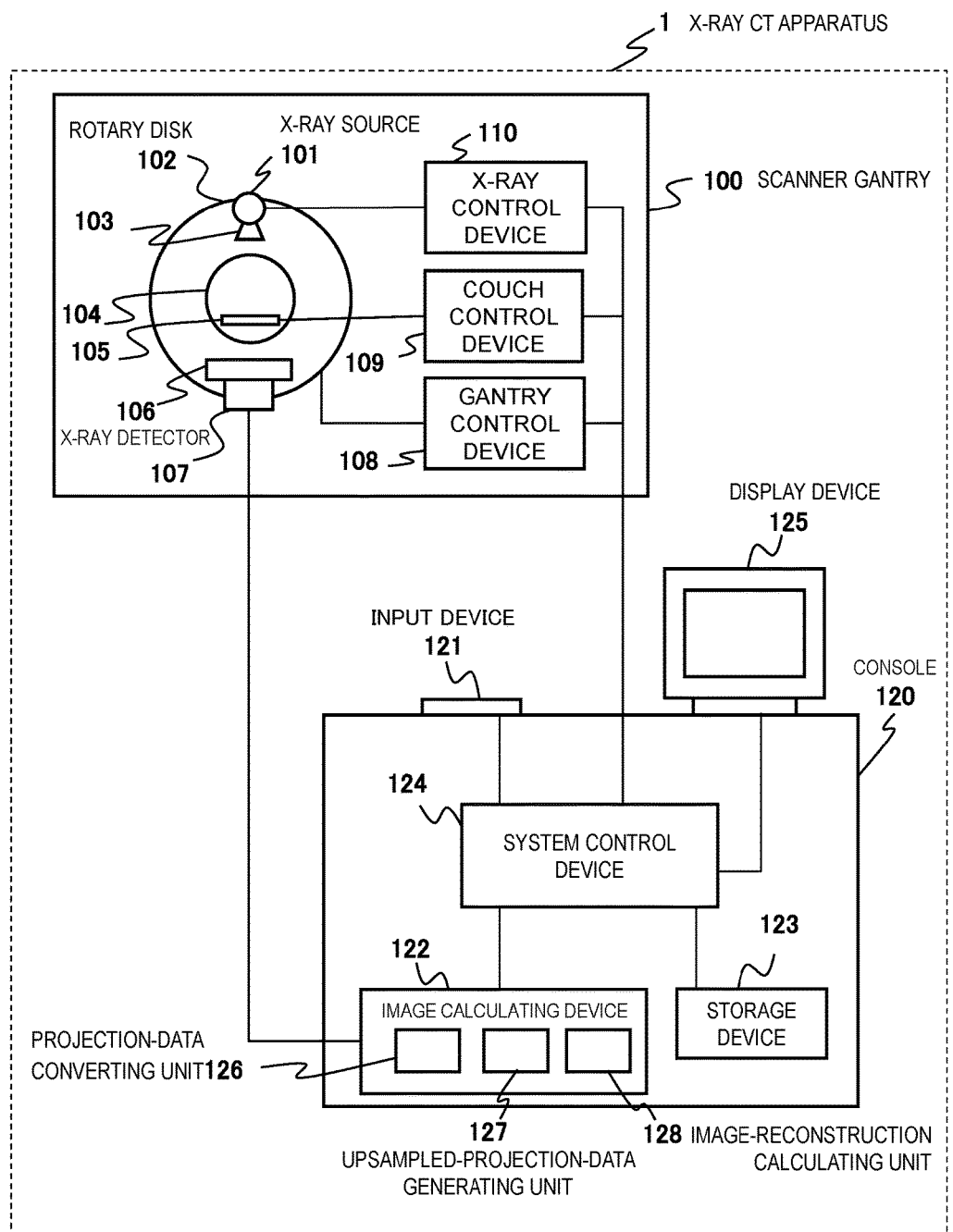
FIG. 1 illustrates a diagram of an entire configuration of an X-ray CT apparatus 1.

As illustrated in FIG. 1, the X-ray CT apparatus 1 includes a scanner gantry 100 and a console 120.

The scanner gantry 100 irradiates an object with X-rays and detects X-rays transmitted through the object. The scanner gantry includes an X-ray tube device (X-ray source) 101, a rotary disk 102, a collimator 103, an X-ray detector 106, a data collecting device 107, a gantry control device 108, a couch control device 109, and an X-ray control device 110.

The rotary disk 102 is provided with an aperture 104, and the X-ray tube device 101 and the X-ray detector 106 are disposed to face each other via the aperture 104. The object positioned on a couch 105 is inserted into the aperture 104. The rotary disk 102 rotates around the object by a drive force that is transmitted through a drive transmitting system from a rotary-disk driving device which is controlled by the gantry control device 108.

The console 120 controls components of the scanner gantry 100, acquires projection data measured by the scanner gantry 100, generates an image, and performs displaying. The console 120 includes an input device 121, an image calculating device 122, a storage device 123, a system control device 124, and a display device 125.

The X-ray tube device 101 is the X-ray source and is controlled by the X-ray control device 110 so as to perform continuous or intermittent irradiation with X-rays having predetermined intensity. The X-ray control device 110 controls an X-ray tube voltage and an X-ray tube current which are applied or supplied to the X-ray tube device 101, depending on an X-ray tube voltage and an X-ray tube current which are determined by the system control device 124 of the console 120.

An X-ray irradiating port of the X-ray tube device 101 is provided with the collimator 103. The collimator 103 limits an irradiation range of X-rays emitted from the X-ray tube device 101. For example, a cone beam (a circular cone-shaped or pyramidal beam) is formed. A width of an opening of the collimator 103 is controlled by the system control device 124.

The transmitted X-rays, which are emitted from the X-ray tube device 101, pass through the collimator 103, and are transmitted through the object, are incident to the X-ray detector 106.

For example, the X-ray detector 106 is provided with about 1,000 X-ray detecting element groups that have a configuration of combining a scintillator and a photodiode and are arranged in a channel direction (revolving direction), and about 1 to 320 element groups that are arranged in a row direction (body-axial direction). The X-ray detector 106 is disposed to face the X-ray tube device 101 via the object. The X-ray detector 106 detects an X-ray dosage transmitted through the object after irradiation is performed from the X-ray tube device 101, and outputs a detected result to the data collecting device 107.

The data collecting device 107 collects, for each view, the X-ray dosages detected by individual X-ray detecting elements of the X-ray detector 106, converts the dosages into digital data, and outputs as transmitted-X-ray data to the image calculating device 122 of the console 120 in order.

The image calculating device 122 acquires the transmitted-X-ray data input from the data collecting device 107, performs preprocessing such as logarithm conversion or sensitivity correction, and generates projection data required for reconstruction.

In addition, the image calculating device 122 includes a projection-data converting unit 126, an upsampled-projection-data generating unit 127, and an image-reconstruction calculating unit 128.

The projection-data converting unit 126 acquires projection data obtained through scanning such as helical scanning or continuous reciprocating scanning for causing the couch 105 and the scanner gantry 100 to relatively move in the body-axial direction while causing the rotary disk 102 to rotate, and converts the acquired data into the projection data obtained by one rotation ($2\pi$) through normal scanning (also referred to as axial scanning) performed at a target slice position. In the following description, the projection data of the normal scanning by one rotation after the conversion is referred to as "normal projection data".

The upsampled-projection-data generating unit 127 inserts (upsamples) a virtual view in the normal projection data using virtual counter data containing counter data acquired on substantially coincident X-ray transmission path on the normal projection data. The virtual counter data acquired on the substantially coincident X-ray transmission path is items of projection data obtained on the closest transmission paths among measured Ray (X-rays) and with the Ray incident in opposite directions. The virtual view is a view inserted between actual views having an actual measurement value. In a case where upsampling is performed by doubling the number of views, one virtual view is inserted between actual views.

Figure 2:
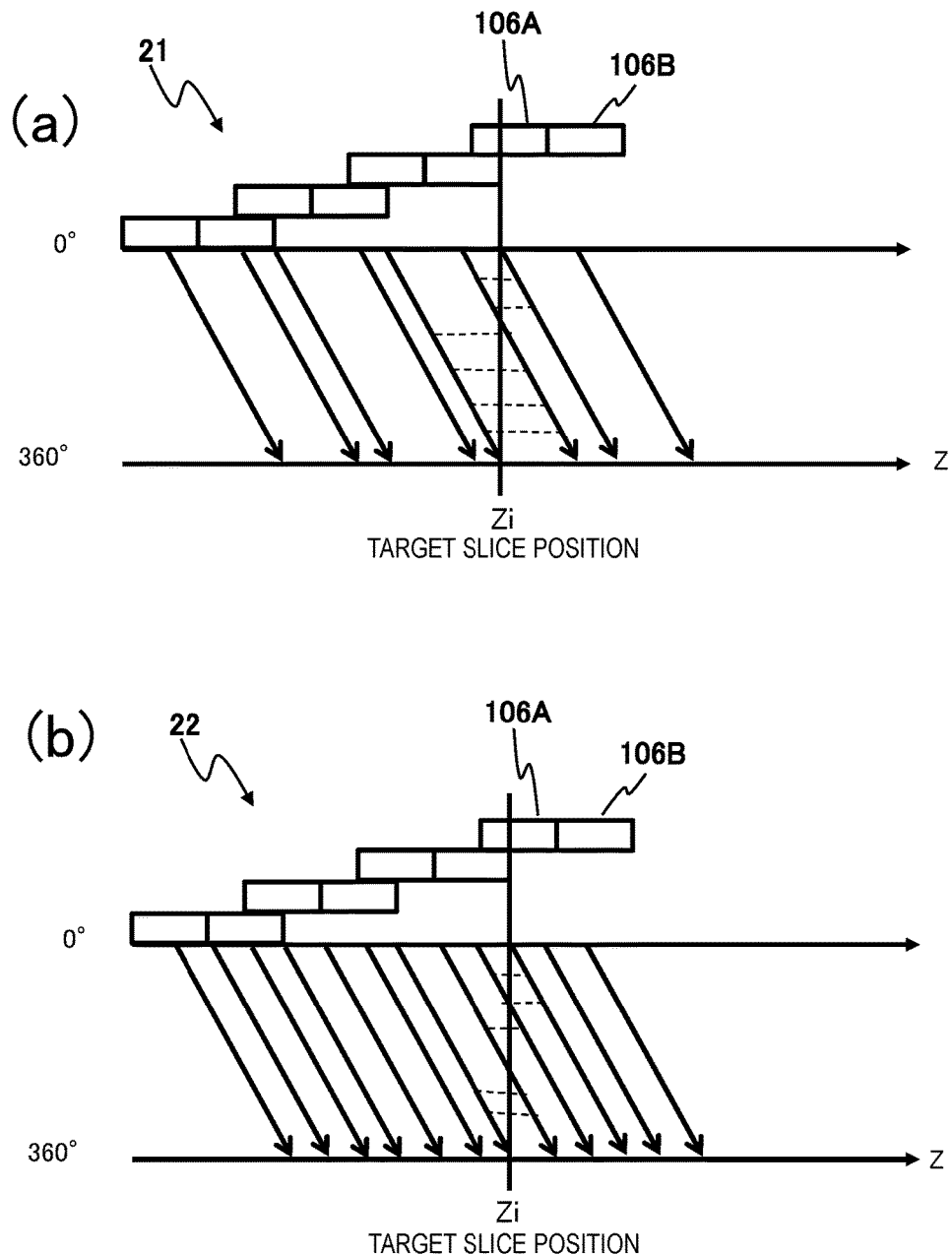
FIG. 2 illustrates diagrams of a method of acquiring projection data at a target slice position in helical scanning.

With reference to FIG. 2, a process of converting the projection data obtained in the helical scanning or the like into projection data (normal projection data) of normal scanning by one rotation ($2\pi$) by the projection-data converting unit 126 at a target slice position is described.

FIG. 2 illustrates scan diagrams 21 and 22 in the helical scanning. In FIG. 2, reference signs 106A and 106B represent X-ray detecting elements in two rows in the X-ray detector 106. The horizontal axes of the scan diagrams 21 and 22 represent a Z axis (body axis), and the vertical axes represent a view.

In the scan diagrams 21 and 22 illustrated in FIG. 2, a projection value at a target slice position Zi is obtained through a 360-degree interpolation method or a 180-degree interpolation method in the case of the helical scanning. In addition, there is known a method in which multiple rows of the X-ray detectors 106 use all of channel interpolation or counter data interpolation in a row direction or filtering (z filtering) in a slice direction, and interpolation of views missing in the helical scanning is performed, compared to views during the normal scanning (during the axial scanning), and the projection data is generated to have the same number of views as those in the normal scanning.

FIG. 2(a) illustrates a case where the channel interpolation in a z direction is not used, and FIG. 2(b) illustrates a case where the channel interpolation in the z direction is used. The projection-data converting unit 126 calculates projection values of views at the target slice position Zi by using a technology such as the channel interpolation in the z direction or the like described above, and converts the normal scanning into equivalent projection data. Normal projection data illustrated in FIG. 3(a) is obtained through such a projection-data converting process.

Figure 3:
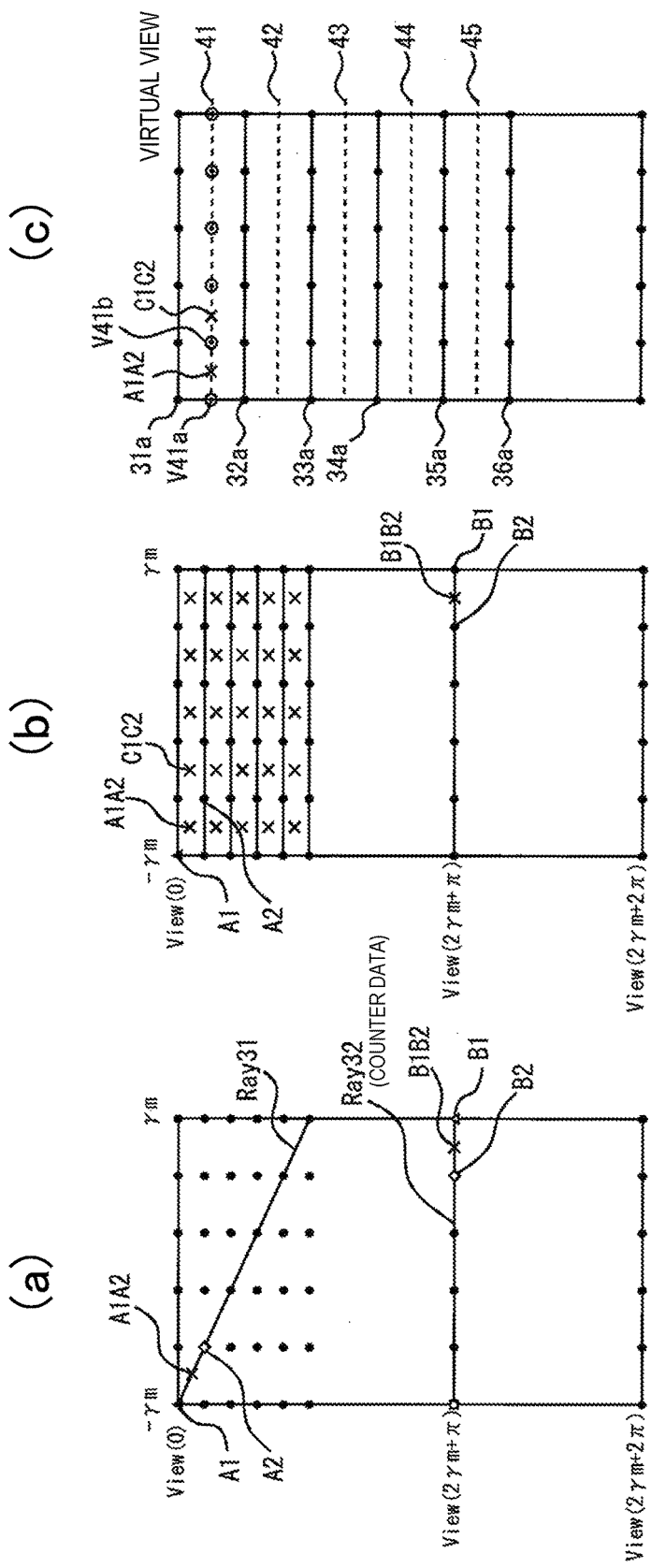
FIG. 3 illustrates diagrams of an upsampling method in which a virtual counter data space is used.

Next, with reference to FIGS. 3 and 4, a process (view-direction upsampling) in which the upsampled-projection-data generating unit 127 doubles the number of views of the normal projection data is described.

In the normal projection data acquired by one rotation illustrated in FIG. 3(a), reference signs Ray31 and Ray32 represent counter data acquired on the substantially coincident X-ray transmission path. In other words, items of counter data of a point A1 and a point A2 on Ray31 correspond to a point B1 and a point B2 on Ray32, respectively. The point B1 and the point B2 are items of data of adjacent channels on the same view view(2γm+π) as illustrated in FIG. 3(a).

A relationship between the point A1 and the point B1 on the projection data can be expressed in the following Expression (1) by using a function R(γ, θ) using a parameter obtained when γ represents the channel direction and θ represents the view direction.

$$R_{A1}(-\gamma_m, 0) = R_{B1}(\gamma_m, 2\gamma_m + \pi) \tag{1}$$

In addition, a relationship between a channel and a view at the point A1 and the point B1 can be expressed in the following expressions (2) and (3).

$$\begin{cases} \gamma_{A1} = -\gamma_{B1} & (2) \\ \theta_{A1} = \theta_{B1} - 2\gamma_{B1} + \pi & (3) \end{cases}$$

In this manner, a point A1A2 in a virtual view 41 between the point A1 and the point A2 is found to correspond to a point B1B2 as a virtual channel inserted between the point B1 and the point B2 on the view view(2γm+π). It is possible to calculate, from the following expressions (4) and (5), a value of a corresponding point (virtual counter data point) A1A2 on the counter data (Ray31) with respect to the virtual channel (point B1B2) on Ray32 (the view view(2γm+π)).

$$\begin{cases} \gamma_{A1A2} = \dfrac{\gamma_{A1} + \gamma_{A2}}{2} = -\left(\dfrac{\gamma_{B1} + \gamma_{B2}}{2}\right) & (4) \\ \theta_{A1A2} = \dfrac{\theta_{A1} + \theta_{A2}}{2} = \left(\dfrac{\theta_{B1} + \theta_{B2}}{2}\right) - 2\left(\dfrac{\gamma_{B1} + \gamma_{B2}}{2}\right) + \pi & (5) \end{cases}$$

In the same procedure, as illustrated in FIG. 3(b), a virtual counter data point C1C2 adjacent to the point A1A2 by one pixel in the virtual view 41 is calculated. A virtual counter data space containing virtual counter data points is generated while iterating the same procedure. As illustrated in FIG. 3(c), a value of a point V41b as a channel position of the virtual view 41 is obtained by interpolation of the virtual counter data points A1A2 and C1C2 on the virtual counter data space. Iteration of such an operation is performed, and thus values of the channels of the virtual view 41 are calculated (points represented by double circles in FIG. 3(c)). Regarding other virtual views 42, 43, and the like, similarly, it is possible to calculate channel data by using the virtual counter data acquired on the substantially coincident X-ray transmission path.

When the operations are iterated, the virtual views 41, 42, 43, and the like are inserted between the actual views.

The projection data upsampled by the upsampled-projection-data generating unit 127 is referred to as upsampled projection data. In particular, upsampled projection data in the view direction is referred to as the view-direction upsampled projection data.

The upsampled-projection-data generating unit 127 outputs the upsampled projection data to the image-reconstruction calculating unit 128.

The image-reconstruction calculating unit 128 reconstructs an image such as a tomogram of an object by using the upsampled projection data. For example, the reconstruction processing of the image may be performed by using either method of a analytical method such as a filtered back projection method or a successive approximation.

The image data reconstructed by the image calculating device 122 (image-reconstruction calculating unit 128) is input to the system control device 124, is stored in the storage device 123, and is displayed by the display device 125.

The system control device 124 is a computer including a central processing unit (CPU), a read only memory (ROM), a random access memory (RAM), or the like. The storage device 123 is a data storage device such as a hard disk, and a program, data, or the like for realizing a function of the X-ray CT apparatus 1 is stored in advance.

Figure 5:
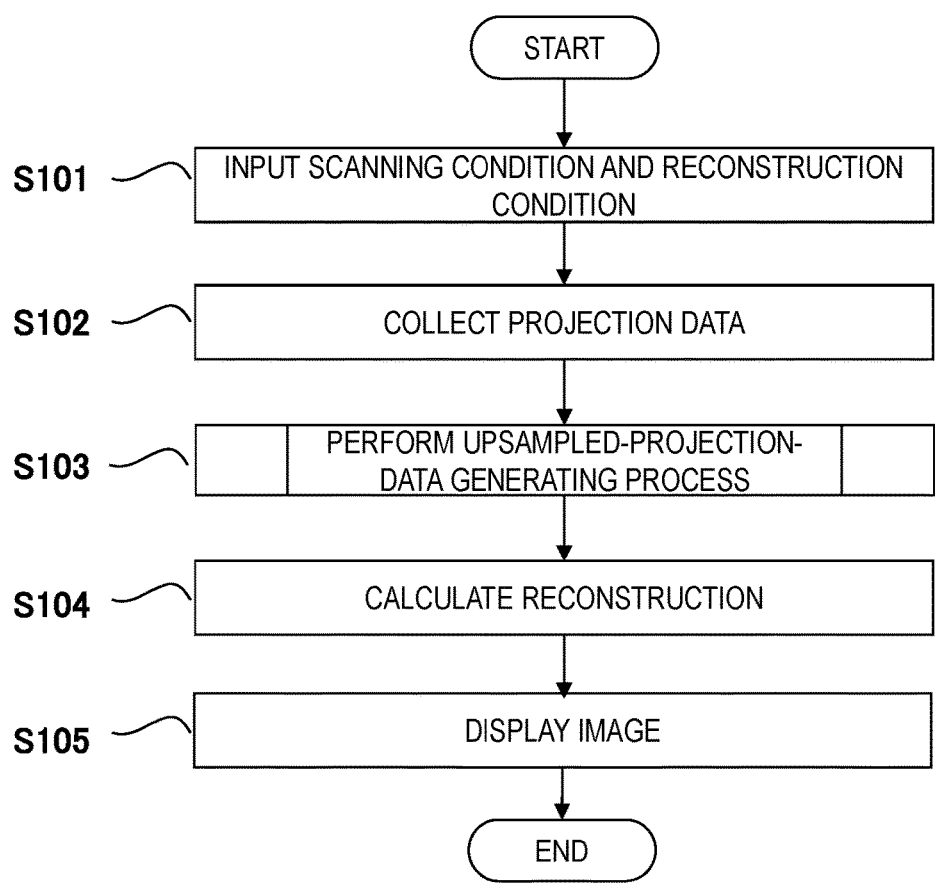
FIG. 5 is a flowchart illustrating flow of overall processes which are performed in the X-ray CT apparatus 1.

The system control device 124 performs scanning process in accordance with a process procedure illustrated in FIG. 5. In the scanning process, the system control device 124 transmits a control signal depending on scanning conditions set by an operator to the X-ray control device 110, the couch control device 109, and the gantry control device 108 of the scanner gantry 100, and controls the devices described above. Details of the processes will be described below in detail.

The display device 125 is configured to include a liquid crystal panel, a display device such as a CRT monitor, and a logic circuit for realizing a display process through linkage to the display device, and is connected to the system control device 124. The display device 125 displays a reconstruction image that is output from the image calculating device 122 and various types of information which are processed in the system control device 124.

The input device 121 is configured to include a keyboard, a pointing device such as a mouse, a numeric keyboard, various switch buttons, or the like, and outputs, to the system control device 124, various types of instructions or information which are input by the operator. The operator operates the X-ray CT apparatus 1 interactively by using the display device 125 and the input device 121. The input device 121 may be a touch panel type input device that is configured to be integral with a display screen of the display device 125.

Next, with reference to FIGS. 5 to 8, operations of the X-ray CT apparatus 1 will be described.

FIG. 5 is a flowchart illustrating flow of overall scanning processes that are performed by the X-ray CT apparatus 1 according to the present invention.

In the scanning process, first, the system control device 124 receives input of scanning conditions and reconstruction conditions. The scanning conditions include X-ray conditions such as an X-ray tube voltage or an X-ray tube current, a range of scanning, a rotating speed of the gantry, a couch speed, or the like. The reconstruction conditions include a reconstruction FOV, a thickness of the reconstruction slice, or the like.

When the scanning conditions and the reconstruction conditions are input via the input device 121 or the like (Step S101), the system control device 124 collects projection data, based on the scanning conditions (Step S102). In other words, the system control device 124 transmits a control signal to the X-ray control device 110, the gantry control device 108, and the couch control device 109, based on the scanning conditions. The X-ray control device 110 controls power that is input to the X-ray tube device 101, based on the control signal that is input from the system control device 124. The gantry control device 108 controls a drive system of the rotary disk 102 in accordance with the scanning conditions such as a rotating speed and causes the rotary disk 102 to rotate. The couch control device 109 positions the couch 105 at a predetermined scanning start position, based on the range of scanning. In addition, it is possible to perform scanning in response to movement of the couch by the couch control device 109 and self-propelling of the gantry by the gantry control device 108.

The irradiation with the X-rays from the X-ray tube device 101 and the measurement of the transmitted-X-ray data by the X-ray detector 106 are iterated along with the rotation of the rotary disk 102 and relative movement of the couch 105 and the scanner gantry 100 with respect to each other. The data collecting device 107 acquires the transmitted-X-ray data measured by the X-ray detector 106 at various angles (views) in a range of the object and transmits the data to the image calculating device 122.

The image calculating device 122 acquires the transmitted-X-ray data input from the data collecting device 107, performs preprocessing such as the logarithm conversion or the sensitivity correction, and generates the projection data.

The image calculating device 122 (projection-data converting unit 126) acquires helical projection data generated in the process in Step S102, performs an interpolation process as illustrated in FIG. 2, and converts the projection data into normal projection data at the target slice position. Then, the image calculating device 122 (upsampled-projection-data generating unit 127) performs an upsampled-projection-data generating process of the projection data obtained after the conversion (Step S103; refer to FIG. 6).

In the upsampled-projection-data generating process, the upsampled-projection-data generating unit 127 inserts (up-samples) virtual views in the projection data obtained after the conversion such that the preset number of views is provided, and generates the view-direction upsampled projection data.

The number of views may be a value set in advance in accordance with the specification of the apparatus or may be a value set by the operator. In addition, the number of views may be a value determined, depending on an image quality index (particularly, spatial resolution) or another parameter set by the operator. The upsampling process will be described below (refer to FIGS. 6 to 8).

When the view-direction upsampled projection data subjected to the upsampling is generated in the process in Step S103, then, the image-reconstruction calculating unit 128 of the image calculating device 122 performs a reconstruction process of the image (Step S104), based on the reconstruction condition input in Step S101. Any types of image reconstruction algorithm used in the reconstruction process of the image may be used. For example, a back projection process such as a Feldkamp method may be used, or the successive approximation or the like may be used.

When the image is reconstructed in Step S104, the system control device 124 displays the reconstructed image on the display device 125 (Step S105), and a series of scanning processes are ended.

Next, the upsampled-projection-data generating process in Step S103 is described with reference to FIG. 6.

Figure 6:
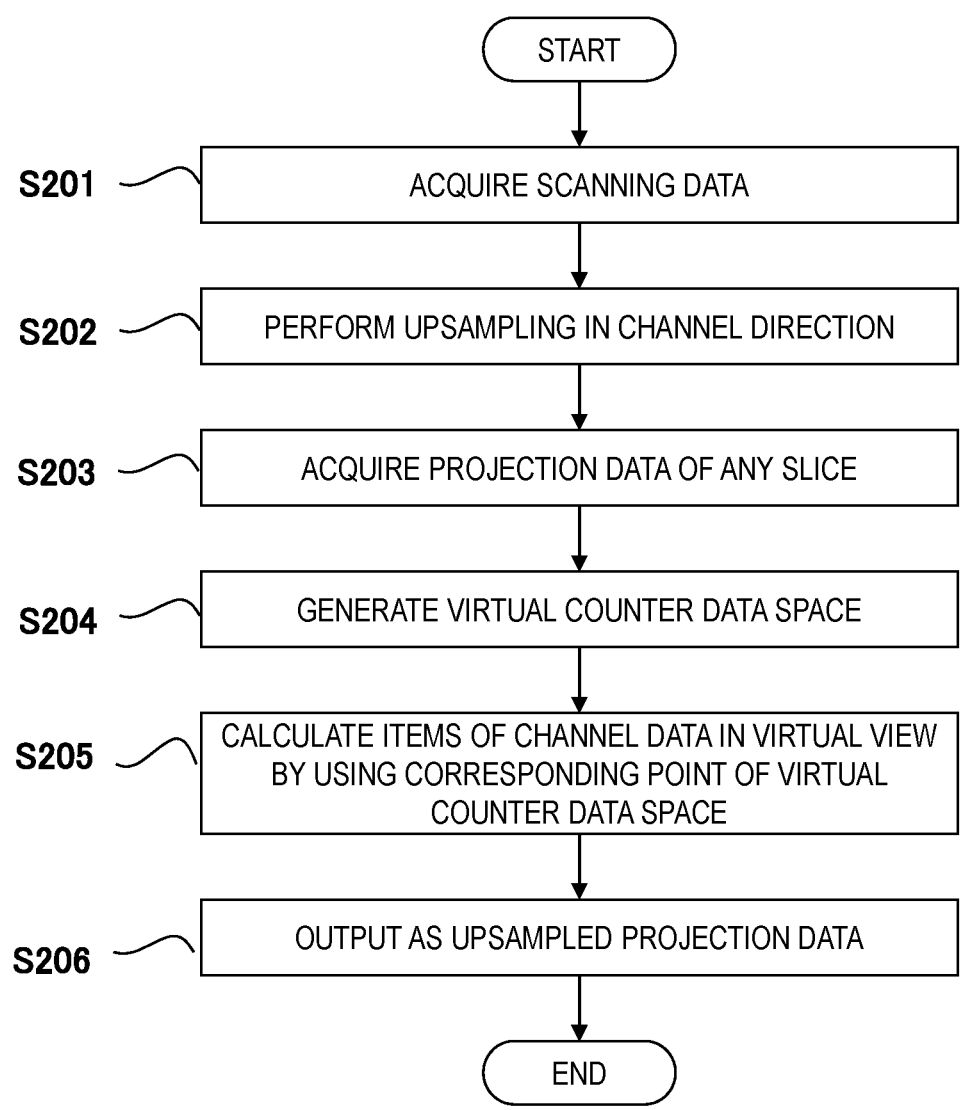
FIG. 6 is a flowchart illustrating a procedure of an upsampling process that is performed by an upsampled-projection-data generating unit 127 of an image calculating device 122.

FIG. 6 is a flowchart illustrating flow of an upsampled-projection-data generating process.

The image calculating device 122 acquires the projection data. The projection data is measured through the helical scanning or the like, and contains normal projection data converted into data obtained by one rotation ($2\pi$) at the target slice position (Step S201). The projection data acquired in Step S201 may be collected by the data collecting device 107 during the scanning or may be measured in advance and stored in the storage device 123 or the like.

Next, the image calculating device 122 performs the upsampling of the views of the acquired normal projection data in the channel direction (Step S202). In other words, the upsampled-projection-data generating unit 127 inserts the virtual channels through the interpolation calculation or the like between channels in an actual view as an actually measured view. In addition, since the channels are arranged in two-dimensional direction (the rotating direction and the body-axial direction) in a multi-row detector, interpolation calculation in two-dimensional direction is performed.

Next, the image calculating device 122 assigns the value of the virtual channel generated in Step S202 to a corresponding point (virtual counter data point) as a virtual view position of the counter data acquired on the substantially coincident X-ray transmission path, and acquires a projection value at any slice (Step S203) after performing the 180-degree interpolation or the 360-degree interpolation or the z filtering.

Next, the image calculating device 122 generates the virtual counter data space (Step S204). In the process in Step S204, the image calculating device 122 obtains, from the projection data, a ray (for example, data as a relationship between Ray31 and Ray32 in FIG. 3(a)) facing the view. The counter data of view($2\gamma m+\pi$) illustrated in FIG. 3(a) is data over a plurality of views and channels as indicated by Ray31. The image calculating device 122 obtains a point (corresponding point A1A2) corresponding to the virtual channel data (point B1B2) described above on the counter data Ray32. The corresponding point (virtual direction data point) is a point positioned between the view and the channel. The image calculating device 122 assigns the value of the point B1B2 to the virtual channel data (value of the point A1A2) described above. The corresponding point A1A2 is referred to as virtual counter data.

When the operation is iterated, the virtual counter data space is generated (FIG. 3(c)). For example, as illustrated in FIG. 3(c), the virtual view 41 is inserted between actual views 31a and 32a. The virtual view 41 is a set of the corresponding points described above. The image calculating device 122 obtains channel data in the virtual view through the interpolation calculation or the like by using the values of the corresponding points (virtual counter data points) in the virtual counter data space (Step S205). For example, the value of the point V41b as the channel position of the virtual view 41 is obtained by interpolation by using the values of the virtual counter data point A1A2 and the corresponding point C1C2 illustrated in FIG. 3(c).

The interpolation calculation in Step S202 or Step S204 may be two-point interpolation performed by interpolation between simply adjacent views as illustrated in FIG. 4(a), or may be four-point interpolation performed by interpolation using data of adjacent views and adjacent channels as illustrated in FIG. 4(b), or may be a total variation (TV) method or the like as illustrated in FIG. 4(c). In addition, linear interpolation or non-linear interpolation may be performed for the two-point interpolation or the four-point interpolation.

The projection data upsampled by the image calculating device 122 (upsampled-projection-data generating unit 127) is referred to as upsampled projection data. The upsampled-projection-data generating unit 127 outputs the upsampled projection data to the image-reconstruction calculating unit 128 (Step S206). The image-reconstruction calculating unit 128 reconstructs an image of the object by using the upsampled projection data.

As described above, the X-ray CT apparatus 1 of the embodiment includes the upsampled-projection-data generating unit 127 that upsamples the projection data. The upsampled-projection-data generating unit 127 acquires the normal projection data obtained by converting the projection data obtained through the helical scanning into the projection data at the target slice position, and inserts (upsamples in the view direction) virtual views by using data of virtual counter data space which is acquired on the substantially coincident X-ray transmission path on the acquired normal projection data.

Since the items of channel data of the virtual view are obtained by using counter data acquired on the substantially coincident X-ray transmission path, it is possible to obtain the items of channel data of the virtual views from the projection data having information of the closest object. In this manner, the upsampled projection data is the data that more approximates to the observed value, and thus it is possible to generate a reliable image. In addition, an effect that a boundary portion is unlikely to be unclear is achieved, compared to a case where the upsampling (simple view interpolation) is performed by using values of adjacent points on the projection data.

Figure 7:
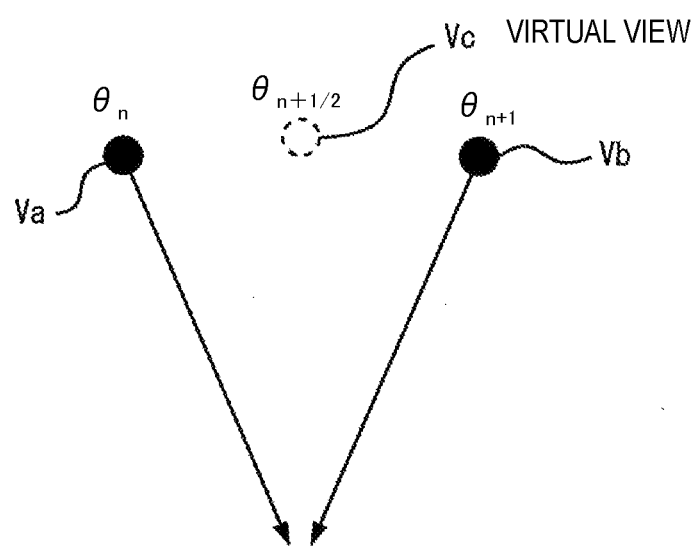
FIG. 7 illustrates a diagram of a positional relationship during measurement between adjacent views Va and Vb and a virtual view Vc.

The effects of the case of using the upsampling method described in the embodiment above is described by using the projection data in FIG. 3(a) as the simplest case with reference to FIGS. 7 and 8.

Points Va and Vb as black circles in FIG. 7 represent adjacent views. $\theta_n$ represents a view position of a view Va, and $\theta_{n+1}$ represents a view position of a view Vb. A virtual view Vc of a dotted-line circle is generated between the views Va and Vb, the upsampling performed through the simple view interpolation and the upsampling employed in the present invention are compared, with a case of doubling the number of views as an example. $\theta_{n+1/2}$ represents a view position of the virtual view Vc.

FIG. 8(a) illustrates the simple view interpolation. In the simple view interpolation, data of the virtual view Vc is interpolated by using the data of the adjacent views Va and Vb. As illustrated in a right figure in FIG. 8(a), this corresponds to interpolation by using data of vertically adjacent points on the projection data. For example, in a case where the number of views is 1500, interpolated data is calculated from data obtained at an interval of 0.24 (360/1500) degree.

FIG. 8(b) illustrates a case where the upsampling is performed by using the technology of the present invention. In the present invention, the value of the virtual channel (point B1B2) inserted between the adjacent actual channels (the point B1 and the point B2) through the interpolation or the like is assigned to the corresponding point (virtual counter data point) at the virtual view position in the virtual counter data space acquired on the substantially coincident X-ray transmission path, and thereby a value of the corresponding point A1A2 close to the virtual view Vc is obtained. Similarly, a value of another corresponding point C1C2 close to the virtual view Vc is obtained from other actual data, and channel data of the virtual view is obtained by using the values of the point A1A2 and the point C1C2.

Hence, it is possible to calculate values of channels of the virtual view by using interpolation data (data represented by "x" in FIG. 8(b)) obtained at a narrower angle, compared to the case of the simple view interpolation illustrated in FIG. 8(a). In other words, it is possible to interpolate data having narrower beam width (shorter distance between the channels), compared to the case of the simple view interpolation, and thus it is possible to obtain an image having high spatial resolution. For example, in a case where a distance between the X-ray tube device 101 and the X-ray detecting element is 1,000 mm, and a distance between the X-ray detecting elements of the X-ray detector 106 in the channel direction is 1 mm, it is possible to obtain channel data in the channel view from data obtained with an inter-channel distance of 0.057 ($=2 \cdot \tan^{-1}((1/2)/1000)$) degree apart.

In addition, according to the present invention, the upsampling in the view direction has an effect of improving spatial resolution in a case where an inter-view distance $\Delta\theta$ is larger, compared to an inter-channel distance $\Delta ch$ (a case of $\Delta\theta > \Delta ch$). Hence, the upsampled-projection-data generating unit 127 uses the simple view interpolation, based on a relationship between the inter-view distance $\Delta\theta$ and the inter-channel distance $\Delta ch$; however, it is desirable to determine that the technology (upsampling method based on the counter data) according to the present invention is performed. Currently, in most of the commonly used X-ray CT apparatuses, a view rate limit is used, and thus the relationship of $\Delta\theta > \Delta ch$ is satisfied.

Otherwise, an appropriate weight may be applied, depending on the relationship of $\Delta\theta > \Delta ch$, to the upsampled projection data acquired by the simple view interpolation and the upsampled projection data acquired by using the counter data of the present invention, and the projection data may be generated by using both of the data.

Further, the example, in which the upsampling is performed with the doubled number of views in the embodiment described above, is described; however, it is possible to increase the upsampling to N times thereof.

In addition, in the embodiment described above, the example, in which the upsampling in the view direction is performed by using the virtual counter data space, is described; however, in the same technology, it is possible to perform the upsampling in the channel direction and the row direction (slice direction).

In the case of performing the upsampling in the channel direction, the upsampled-projection-data generating unit 127 inserts the virtual view data between the actual channels by using the acquired projection data, and assigns the value of the virtual view data to the value of the corresponding point at the virtual channel position of the points in the virtual counter data space acquired on the substantially coincident X-ray transmission path. The view data in the virtual channel is calculated by using the values of the corresponding points and the upsampled projection data in the channel direction is generated.

Figure 9:
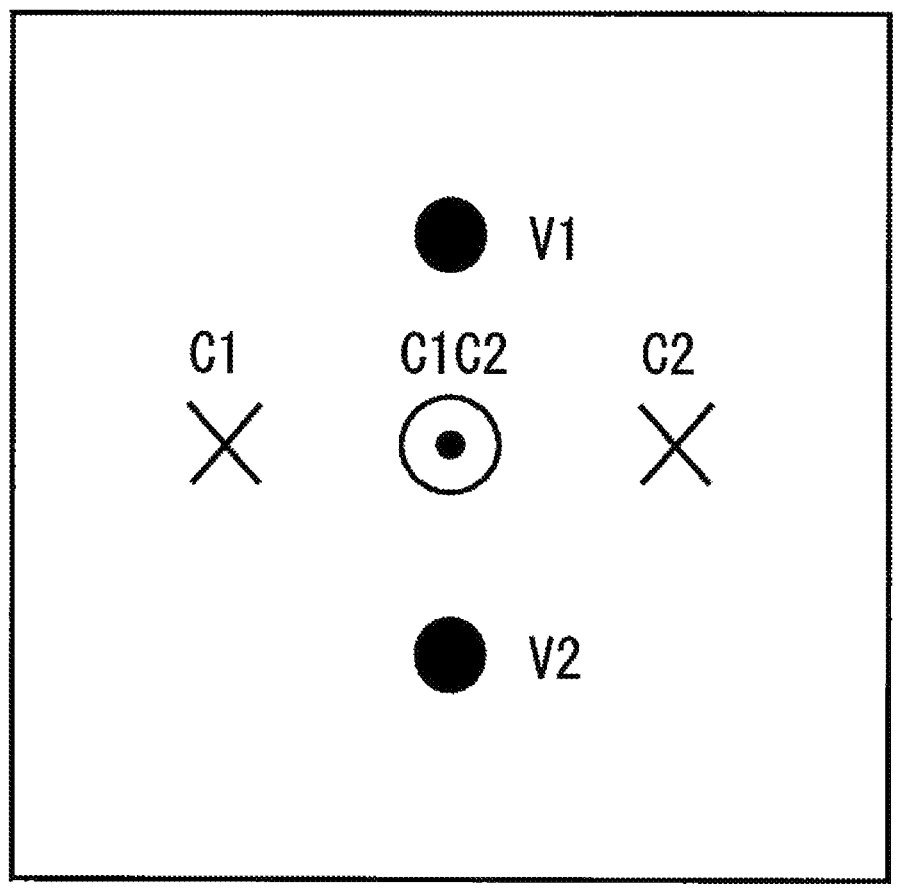
FIG. 9 illustrates a diagram of upsampling in a channel direction.

An example of the upsampling in the channel direction is described with reference to FIG. 9. FIG. 9 illustrates partially cut-out projection data similar to FIGS. 4(a) to 4(c), points C1 and C2 represent actual projection data, and points V1 and V2 represent virtual projection data obtained through the interpolation process or the like. A value of a point C1C2 is obtained by using values of the points C1, C2, V1 and V2.

For example, the value of the point C1C2 may be obtained by performing interpolation calculation in Expression (6), using a weight coefficient obtained in the inter-view distance $\Delta\theta$ and the inter-channel distance $\Delta ch$.

$$C1C2 = W_{c1} \cdot C1 + W_{c2} \cdot C2 + W_{v1} \cdot V1 + W_{v2} \cdot V2 \tag{6}$$

Here, $W_{c1}$, $W_{c2}$, $W_{v1}$, and $W_{v2}$ represent a weight coefficient that satisfies Expression (7).

$$W_{C1} + W_{C2} + W_{V1} + W_{V2} = 1 \tag{7}$$

The weight coefficients $W_{c1}$, $W_{c2}$, $W_{v1}$, and $W_{v2}$ are obtained by Expressions (8) and (9), depending on the relationship between the inter-view distance $\Delta\theta$ and the inter-channel distance $\Delta ch$.

$$W_{C1} = W_{C2} = \Delta\theta/(2(\Delta\theta + \Delta ch)) \tag{8}$$

$$W_{V1} = W_{V2} = \Delta ch/(2(\Delta\theta + \Delta ch)) \tag{9}$$

In addition, the upsampling in the channel direction is described; however, the interpolation calculation using Expressions (6) to (9) may also be performed in the upsampling in the view direction or the slice direction.

It is also possible to apply the upsampling method according to the present invention described above to the projection data obtained through any projection data. For example, the upsampling method may be also applied to flying focus spot (FFS) projection data or quarter offset projection data. The FFS projection data means projection data obtained by scanning performed while the focus position in the X-ray tube moves to a plurality of positions. The quarter offset projection data means projection data obtained with a half (doubling of the number of channels) of channel intervals, with the X-ray detector 106 disposed at a shifted position by one fourth of the element in the rotating direction (channel direction) of the rotary disk 102 from the center of the irradiation of the X-rays and by combining the acquired data in the counter view.

Second Embodiment

Next, a second embodiment of the present invention will be described.

In the second embodiment, an example, in which the upsampling using the virtual counter data space described in the first embodiment is applied to FFS projection data, is described.

In recent years, an FFS X-ray tube device having a function of causing the X-ray focus to a plurality of positions and performing irradiation with the X-rays is developed. In the FFS X-ray tube device, a position of an electron beam incident to an anode (target) is caused to electromagnetically move, and thereby it is possible to cause the X-ray focus position to shift to a plurality of positions. In this manner, since it is possible to obtain a plurality of items of projection data obtained on different X-ray irradiating paths in the same rotating angle direction (view), it is possible to improve the spatial resolution of the X-ray CT apparatus (FFS method).

Incidentally, the reconstructed image by using the FFS method in the related art is improved in the spatial resolution in the vicinity of the center in an entire effective field of view; however, a problem arises in that the spatial resolution decreases in a peripheral portion other than the central portion. By comparison, PTL 1 proposes a balanced flying focus spot (BFFS) method in which the optimal focus shifting distance is set, based on the number of views (an angle difference in adjacent views) through the scanning by one rotation and a distance between rotating centers of the X-ray tube device, and thereby even spatial resolution or improvement in the spatial resolution is achieved in the peripheral portion.

However, the sampling rate or the gantry rotating speed of the data collecting device is limited due to the hardware limit. In order to increase the number to views through the scanning by one rotation, it is necessary to decrease the rotating speed of the gantry. In a case where the number of views increases due to a decrease in the rotating speed, motion artifacts are likely to increase in an internal organ having fast movement, such as a heart. The more the motion artifacts influence the image, the faster movement the internal organ has. Thus, it is inconvenient for a radiologist who performs the diagnostic imaging. Therefore, in the scanning of a target portion with movement, it is desirable to improve the spatial resolution over the entire effective field of view without decreasing the rotating speed.

In the second embodiment, an X-ray CT apparatus and an image reconstruction method of improving the spatial resolution of the entire effective field of view without a decrease in the rotating speed even during the helical scanning or the continuous reciprocating scanning, in the FFS method of improving the spatial resolution by obtaining the projection data through causing the X-ray focus position to move to a plurality of positions are described.

Figure 10:
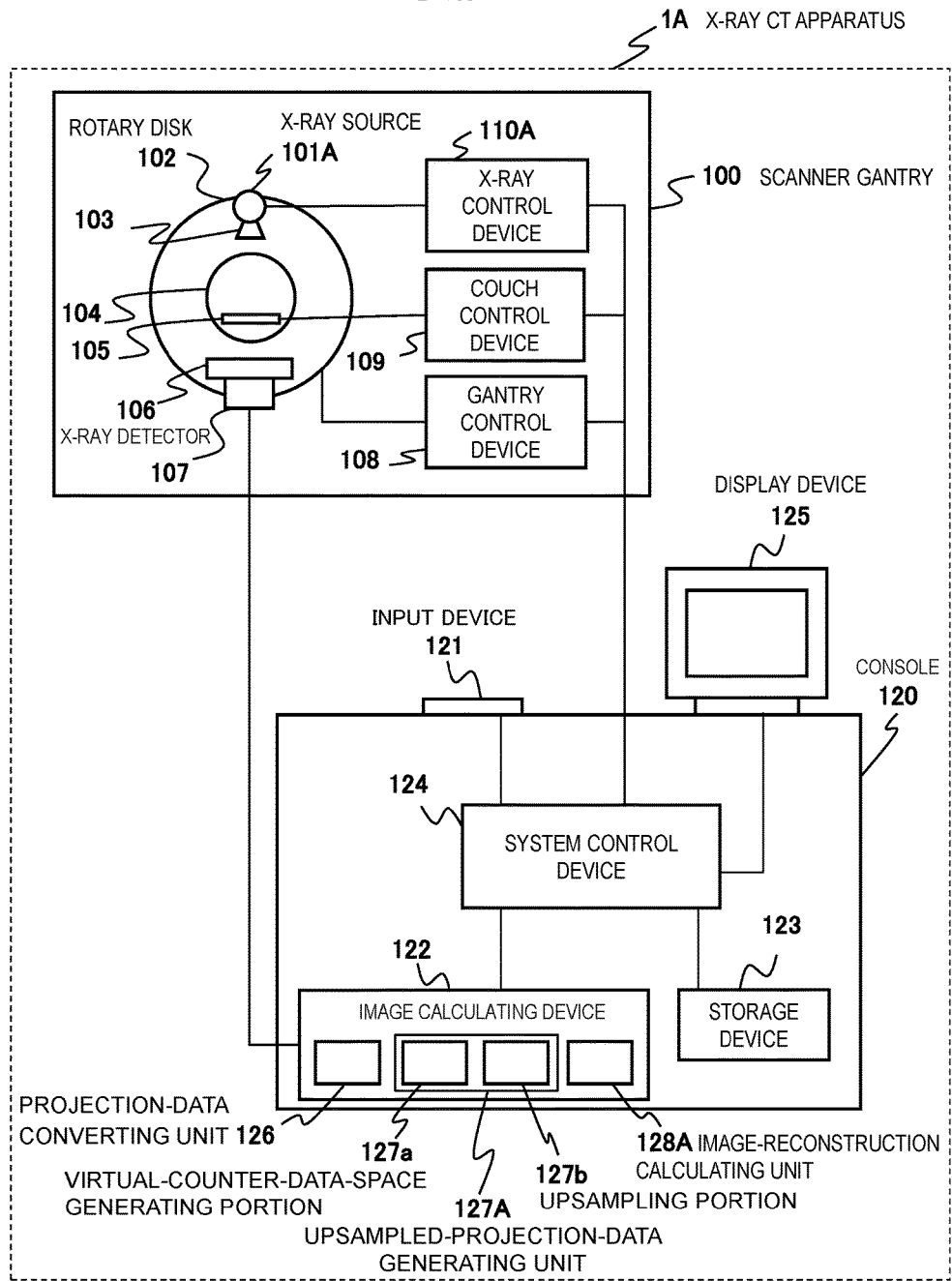
FIG. 10 illustrates a diagram of an entire configuration of an X-ray CT apparatus 1A of a second embodiment.

FIG. 10 illustrates a diagram of a configuration of an X-ray CT apparatus 1A of a second embodiment. As illustrated in FIG. 10, the X-ray CT apparatus 1A includes a scanner gantry 100 and a console 120. In the following description, the same reference signs are assigned to the same configurations as the components of the X-ray CT apparatus 1 of the first embodiment, and repeated description thereof is omitted.

The scanner gantry 100 includes an X-ray tube device (X-ray source) 101A, the rotary disk 102, the collimator 103, the X-ray detector 106, the data collecting device 107, the gantry control device 108, the couch control device 109, and an X-ray control device 110A.

The X-ray tube device 101A is a flying focus X-ray tube device that is capable of causing a focus position to move on a rotary anode (target). When the rotation-axis direction of the X-ray CT apparatus 1A is set to the Z direction, the flying focus X-ray tube device biases the electron beam, with which the rotary anode (target) is irradiated, in an X direction or a Y direction which is orthogonal to the Z direction. In this manner, the X-ray focus position is caused to shift and irradiation with an X-ray having a path slightly different from the same view position is performed.

In the embodiment, a movement direction of the focus by the X-ray tube device 101A is set to the rotating direction (channel direction) of the X-ray CT apparatus 1A. In addition, the position of the focus becomes a position shifted by "+σa" and "−σb" in the rotating direction (channel direction) from a reference focus position. In other words, the X-ray tube device 101 performs the irradiation with X-rays from a first focus position "+σa" shifted in a positive direction of the channel direction and a second focus position "−σb" shifted in a negative direction thereof, respectively.

In the following description, the projection data obtained by using the FFS method is referred to as FFS projection data. In particular, the projection data obtained through the irradiation with the X-rays from the first focus position described above is referred to as FFS(+) projection data, and the projection data obtained through the irradiation with the X-rays from the second focus position described above is referred to as FFS(−) projection data. In addition, the projection data obtained through the irradiation with the X-rays from the reference focus position without using the FFS technology is referred to as FFS(NO) projection data.

The X-ray tube device 101A is controlled by the X-ray control device 110A so as to perform continuous or intermittent irradiation with X-rays having predetermined intensity. The X-ray control device 110A controls the X-ray tube voltage and the X-ray tube current which are applied or supplied to the X-ray tube device 101A, depending on the X-ray tube voltage and the X-ray tube current which are determined by the system control device 124 of the console 120. The X-ray control device 110A controls to cause the first and second focus positions described above to alternately shift for each view in response to the rotation of the rotary disk 102.

An image calculating device 122A acquires the transmitted-X-ray data input from the data collecting device 107, performs preprocessing such as the logarithm conversion or the sensitivity correction, and generates the projection data required for reconstruction. In a case of using the FFS method, since irradiation with the X-rays having focuses alternately different for each view is performed from the X-ray tube device 101A, the image calculating device 122A generates the FFS(+) projection data as the projection data obtained through the irradiation with the X-rays from the first focus position and the FFS (−) projection data as the projection data obtained through the irradiation with the X-rays from the second focus position.

In addition, the image calculating device 122A includes the projection-data converting unit 126, an upsampled-projection-data generating unit 127A, and an image-reconstruction calculating unit 128A. The upsampled-projection-data generating unit 127A includes a virtual-counter-data-space generating portion 127a and an upsampling portion 127b.

The upsampled-projection-data generating unit 127A generates virtual views with respect to focus-shifted projection data (the FFS(+) projection data and the FFS(−) projection data) obtained through the scanning by using the FFS method, and generates the upsampled projection data by the insertion. The virtual view is the view inserted through the calculation at a view position that is not actually scanned. It is possible to obtain the projection data of the virtual view by interpolation or estimation, based on the projection data (hereinafter, referred to as actual data) obtained through the actual scanning.

The virtual-counter-data-space generating portion 127a generates, through the same technique as that in the first embodiment, the virtual counter data space of the projection data (normal FFS(+) projection data and normal FFS(−) projection data) as a processing target.

The upsampling portion 127b increases the number of views by combining the FFS(+) projection data and the FFS(−) projection data. Otherwise, the number of views is further increased by combining the FFS projection data at focus positions with the increased number of views.

The generation of the upsampled projection data by the virtual-counter-data-space generating portion 127a and the upsampling portion 127b will be described below in detail. The projection data generated (upsampled) by the upsampled-projection-data generating unit 127A is referred to as the upsampled projection data.

The projection-data converting unit 126 converts projection data (helical projection data) collected by causing the couch 105 and the scanner gantry 100 to relatively move in the body-axial direction while causing the rotary disk 102 to rotate, which is obtained through the helical scanning, the continuous reciprocating scanning, or the like, into normal projection data as the projection data obtained by one rotation ($2\pi$) at the target slice position. The 360-degree interpolation, the 180-degree interpolation, the z filter process, or the like is applied as illustrated in FIG. 2 to the projection data obtained by the helical scanning or the like described above, and thereby the normal projection data is obtained at the target slice position. In the following description, data obtained by converting helical FFS(+) projection data into the normal projection data at the target slice position is referred to as normal FFS (+) projection data, and data obtained by converting helical FFS (−) projection data into the normal projection data at the target slice position is referred to as normal FFS(−) projection data.

The image-reconstruction calculating unit 128A reconstructs an image such as a tomogram of an object by using the projection data (the normal FFS (+) projection data and the normal FFS (−) projection data) obtained before the upsampling process (insertion of the virtual views) is performed and the upsampled projection data generated by the upsampled-projection-data generating unit 127A. In the following description, the projection data (the normal FFS (+) projection data and the normal FFS (−) projection data) obtained before the upsampling process (insertion of the virtual views) is performed, is referred to as the "actual data".

In the embodiment, the image-reconstruction calculating unit 128A reconstructs the image by using the actual data (the FFS (+) projection data and the FFS (−) projection data) and the upsampled projection data in consideration of the spatial resolution of the image. Specifically, the image is reconstructed by using the actual data in the central region in the image plane, and thereby the spatial resolution of the central region improves. In addition, the image is reconstructed by using the upsampled projection data in the peripheral region in the image, and thereby the spatial resolution improves. In other words, the spatial resolution in the peripheral region is likely to decrease in a case where the actual data of the FFS projection data is used in the entire region of the image; however, in the embodiment, improvement in the spatial resolution in the peripheral region is achieved by using the upsampled projection data in the peripheral region. It is possible to increase the number of views of the upsampled projection data without decreasing the rotating speed in order to insert the virtual view through the calculation. Hence, this is particularly preferable in a case where an image of a portion with motion is generated.

For example, the reconstruction processing of the image may be performed by using either method of an analytical method such as a filtered back projection method or a successive approximation.

The image data reconstructed by the image calculating device 122A (image-reconstruction calculating unit 128A) is input to the system control device 124, is stored in the storage device 123, and is displayed by the display device 125.

Figure 11:
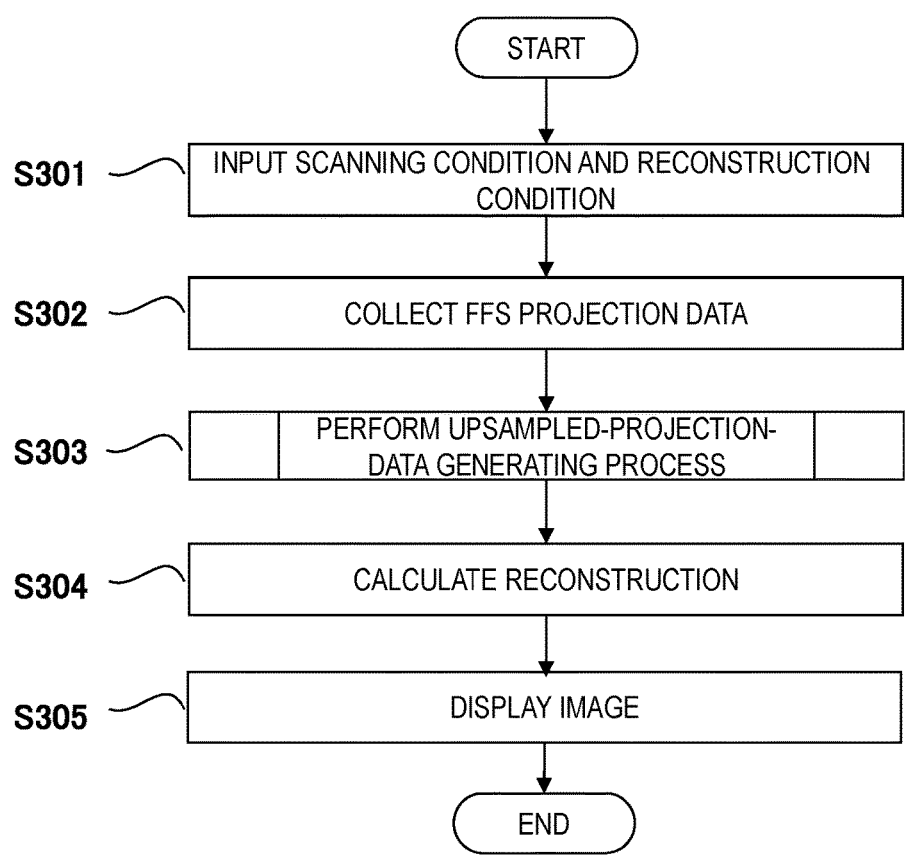
FIG. 11 is a flowchart illustrating flow of overall processes which are performed in the X-ray CT apparatus 1A.

The system control device 124 performs scanning process in accordance with a process procedure illustrated in FIG. 11. In the scanning process, the system control device 124 transmits a control signal depending on scanning conditions set by an operator to the X-ray control device 110A, the couch control device 109, and the gantry control device 108 of the scanner gantry 100, and controls the devices described above. Details of the processes will be described below.

Next, operations of the X-ray CT apparatus 1A will be described.

FIG. 11 is a flowchart illustrating flow of overall scanning processes that are performed by the X-ray CT apparatus 1A of the second embodiment according to the present invention.

In the scanning process, first, the system control device 124 receives input of scanning conditions and reconstruction conditions. The scanning conditions include X-ray conditions such as an X-ray tube voltage or an X-ray tube current, a range of scanning, a rotating speed of the gantry, a couch speed, or the like. The reconstruction conditions include a reconstruction FOV, a thickness of the reconstruction slice, or the like.

When the scanning conditions and the reconstruction conditions are input via the input device 121 or the like (Step S301), the system control device 124 transmits a control signal to the X-ray control device 110A, the gantry control device 108, and the couch control device 109, based on the scanning conditions. The X-ray control device 110A controls power that is input to the X-ray tube device 101A, based on the control signal that is input from the system control device 124. In addition, the X-ray control device 110A causes the electron beam, with which the rotary anode of the X-ray tube device 101A is irradiated, to move by a predetermined direction and a distance at a predetermined timing, and thereby the FFS control of performing irradiation with the X-rays by causing the X-ray focus positions to alternately move is performed. The gantry control device 108 controls a drive system of the rotary disk 102 in accordance with the scanning conditions such as a rotating speed, and causes the rotary disk 102 to rotate.

The couch control device 109 positions the couch at a predetermined scanning start position, based on the range of scanning. Then, the system control device 124 starts scanning. The scanning includes scanning according to movement of the couch controlled by the couch control device 109, self-propelling of the gantry controlled by the gantry control device 108, or the movement of both devices. In other words, the system control device 124 performs the helical scanning, the continuous reciprocating scanning, or the like.

The irradiation with the X-rays from the X-ray tube device 101A and the measurement of the transmitted-X-ray data by the X-ray detector 106 are iterated along with the rotation of the rotary disk 102 and relative movement of the couch 105 and the scanner gantry 100 with respect to each other. The data collecting device 107 acquires the transmitted-X-ray data measured by the X-ray detector 106 at various angles (views) in a range of the object and transmits the data to the image calculating device 122A. The image calculating device 122A acquires the transmitted-X-ray data input from the data collecting device 107, performs preprocessing such as the logarithm conversion or the sensitivity correction, and generates the projection data. In the second embodiment, since the scanning is performed by causing the X-ray focus position to move to two points by using the FFS method, the image calculating device 122A generates the FFS(+) projection data as the projection data obtained through the irradiation with the X-rays from the first focus position and the FFS (−) projection data as the projection data obtained through the irradiation with the X-rays from the second focus position (Step S302).

The image calculating device 122A (projection-data converting unit 126) converts the FFS(+) projection data and the FFS(−) projection data into the normal FFS(+) projection data and the normal FFS (−) projection data at the target slice position.

The image calculating device 122A (upsampled-projection-data generating unit 127A) performs the upsampled-projection-data generating process (Step S303) by using the FFS (+) projection data and the FFS (−) projection data (collectively referred to as FFS projection data) generated in the process in Step S302.

In the upsampled-projection-data generating process, the upsampled-projection-data generating unit 127A inserts (upsamples) virtual views in the actual data such that the preset number of views is provided, and generates the upsampled projection data. The number of views may be a value set in advance in accordance with the specification of the apparatus or may be a value set by the operator. In addition, the number of views may be a value determined, depending on an image quality index (particularly, spatial resolution) or another parameter set by the operator. A specific method of the upsampled-projection-data generating process will be described in detail (refer to FIGS. 12 to 19).

When the upsampled projection data obtained by inserting the virtual views is generated in the process in Step S303, then, the image-reconstruction calculating unit 128A of the image calculating device 122A performs a reconstruction process of the image (Step S304), based on the reconstruction conditions input in Step S301. Any types of image reconstruction algorithm used in the reconstruction process of the image may be used. For example, a back projection process such as a Feldkamp method may be used, or the successive approximation or the like may be used.

The spatial resolution of the image which is reconstructed by using the FFS projection data is high in the central region of the image, compared to a case where the FFS projection data is not used, and is lower than in a case where the projection data without FFS is used at a position close to the periphery (refer to FIG. 21). In the reconstruction calculation process in Step S304 in the present invention, the projection data subjected to the upsampling with the virtual views is used in a region (low region; a peripheral region) with low spatial resolution without the effects of the FFS. The image is reconstructed by using the actual data of the FFS projection data in a region (Hi region; central region) with the effects of the FFS. Details of the reconstruction processes will be described below.

When the image is reconstructed in Step S304, the system control device 124 displays the reconstructed image on the display device 125 (Step S305), and a series of scanning processes are ended.

Next, regarding the upsampled-projection-data generating process in Step S303, aspects of upsampled-projection-data generating processes (A) to (D) are described with reference to FIGS. 12 to 20.

First, the upsampled-projection-data generating process (A) is described with reference to FIGS. 12 and 13. In the following description, FFS(+) projection data 501 and FFS (−) projection data 502 are described as data obtained by converting the FFS(+) projection data 501 and the FFS(−) projection data 502 obtained through the helical scanning or the like into projection data (the normal FFS(+) projection data 501 and the normal FFS(−) projection data 502) at the target slice position.

When the image calculating device 122A acquires the FFS(+) projection data 501 and the FFS(−) projection data 502 which are obtained by causing the focus of the X-ray tube device 101A to move (Step S401), the FFS projection data 503 is obtained by combining the FFS(+) projection data 501 and the FFS(−) projection data 502 alternately in the view direction (Step S402). Further, a virtual view generating process 504 is performed on the FFS projection data 503 (Step S403), and upsampled projection data 505 is obtained. In Step S403, the virtual view generating process 504 performed by the image calculating device 122A performs the virtual-counter-data generating process and the upsampling process, thereby obtaining the upsampled projection data 505. The upsampled-projection-data generating unit 127A outputs the upsampled projection data 505 to the image-reconstruction calculating unit 128A (Step S404).

Here, the FFS(+) projection data 501 and the FFS(−) projection data 502 described above contain the projection data measured by causing the couch 105 and the scanner gantry 100 to relatively move in the body-axis direction while causing the rotary disk to rotate through the helical scanning, the continuous reciprocating scanning, multiple continuous scanning, or the like. In addition, the projection data may contain the projection data obtained through synchronized scanning in which the scanning is performed while a living body signal is achieved by using a scanning synchronization device. The scanning synchronization device measures the living body signal using a respiratory meter, an electrocardiograph, pulse wave system, synchronizes with the motion of the object obtained based on the living body signal, and controls the scanning.

The upsampled-projection-data generating process (B) is described with reference to FIGS. 14 and 15.

When the image calculating device 122A acquires the FFS(+) projection data 501 and the FFS(−) projection data 502 which are obtained by causing the focus of the X-ray tube device 101A to move (Step S501), the virtual view generating process 504 described above is performed on the FFS (+) projection data 501 and the FFS(−) projection data 502 (Step S502). FFS projection data 513 is obtained by combining the upsampled FFS(+) projection data 511 and FFS(−) projection data 512 alternately in the view direction (Step S503). The upsampled-projection-data generating unit 127A outputs the upsampled projection data 513 to the image-reconstruction calculating unit 128A (Step S504).

The upsampled-projection-data generating process (C) is described with reference to FIGS. 16 and 17.

When the image calculating device 122A acquires the FFS (+) projection data 501 and the FFS (−) projection data 502 which are obtained by causing the focus of the X-ray tube device 101A to move (Step S601), the virtual view generating process 504 described above is performed on the FFS (+) projection data 501 and the FFS(−) projection data 502 (Step S602). The upsampled FFS projection data 513 is obtained by combining the upsampled FFS (+) projection data 511 and the FFS (−) projection data 512 alternately in the view direction (Step S603).

The upsampled-projection-data generating unit 127A further performs a missing data process 514 on the upsampled FFS projection data 513 (Step S604).

The missing data process means a process of filling the missing data occurring in the FFS projection data 513 obtained by combining the FFS(+) projection data and the FFS(−) projection data alternately in the view direction through the interpolation or the estimation by using adjacent projection data in the view direction and the channel direction or the close projection data. The FFS(+) projection data and the FFS (−) projection data obtained by causing the focus position to shift in the channel direction have different X-ray paths, respectively. Therefore, data of doubling the number of channels is obtained. In a case where the focus positions are caused to alternately move for each view during the scanning and the projection data is measured, the FFS (+) projection data is acquired in an odd number of views, and the FFS (−) projection data is acquired in an even number of views. Therefore, in the FFS projection data 513 obtained by combining the data alternately, the missing data occurs alternately for each view.

In the process in Step S604, the process 514 of filling with the missing data is performed.

When the upsampled projection data 515 subjected to the missing data process 514 of Step S604 is obtained, the upsampled-projection-data generating unit 127A outputs the upsampled projection data 515 to the image-reconstruction calculating unit 128A (Step S605).

The upsampled-projection-data generating process (D) is described with reference to FIGS. 18 and 19.

When the image calculating device 122A acquires the FFS (+) projection data 501 and the FFS (−) projection data 502 which are obtained by causing the focus of the X-ray tube device 101A to move (Step S701), the virtual view generating process 504 described above is performed on the FFS (+) projection data 501 and the FFS(−) projection data 502 (Step S702). The upsampled FFS projection data 513 is obtained by combining the upsampled FFS (+) projection data 511 and FFS (−) projection data 512 alternately in the view direction (Step S703).

The upsampled-projection-data generating unit 127A further performs the virtual view generating process 504 described above on the upsampled FFS projection data 513 (Step S704). The upsampled projection data 516 is obtained through the process in Step S704.

The upsampled-projection-data generating unit 127A outputs the upsampled projection data 516 to the image-reconstruction calculating unit 128A (Step S705).

Figure 12:
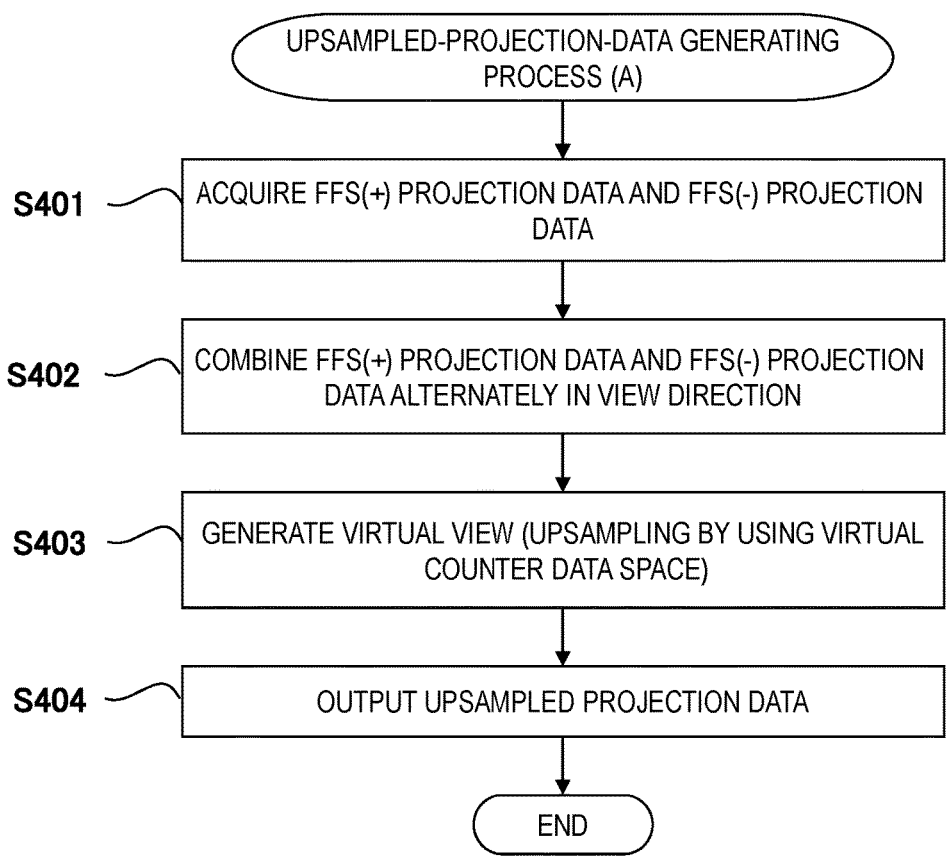
FIG. 12 is a flowchart illustrating flow of an upsampled-projection-data generating process (A).
Figure 14:
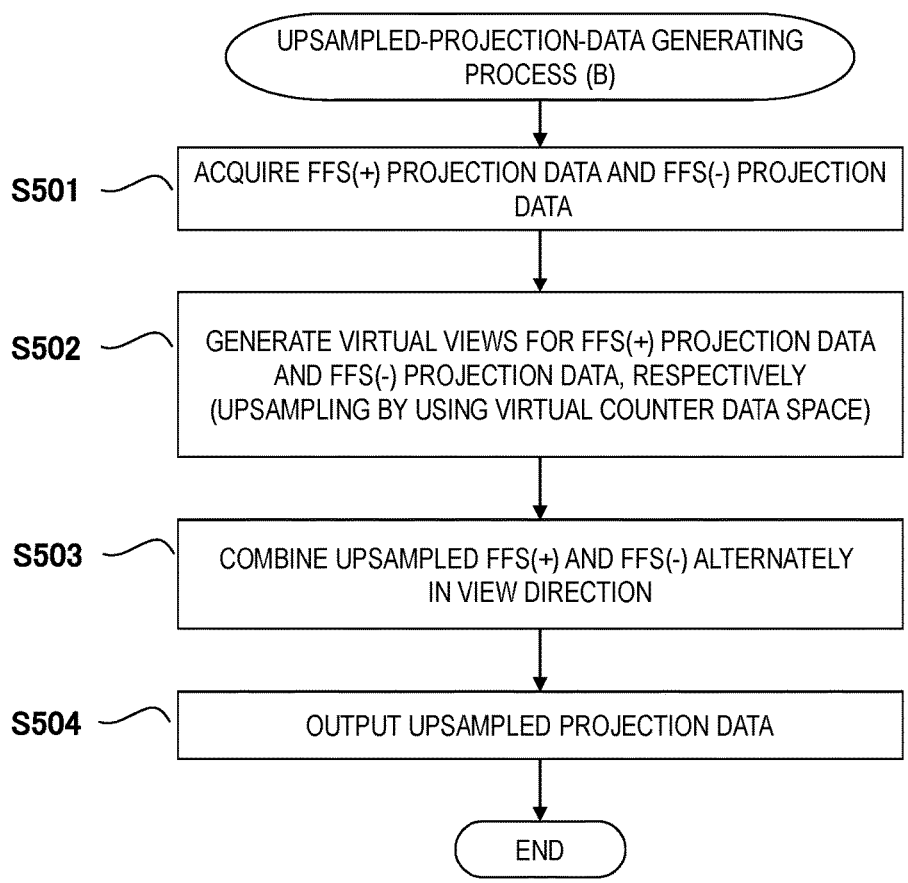
FIG. 14 is a flowchart illustrating flow of an upsampled-projection-data generating process (B).
Figure 16:
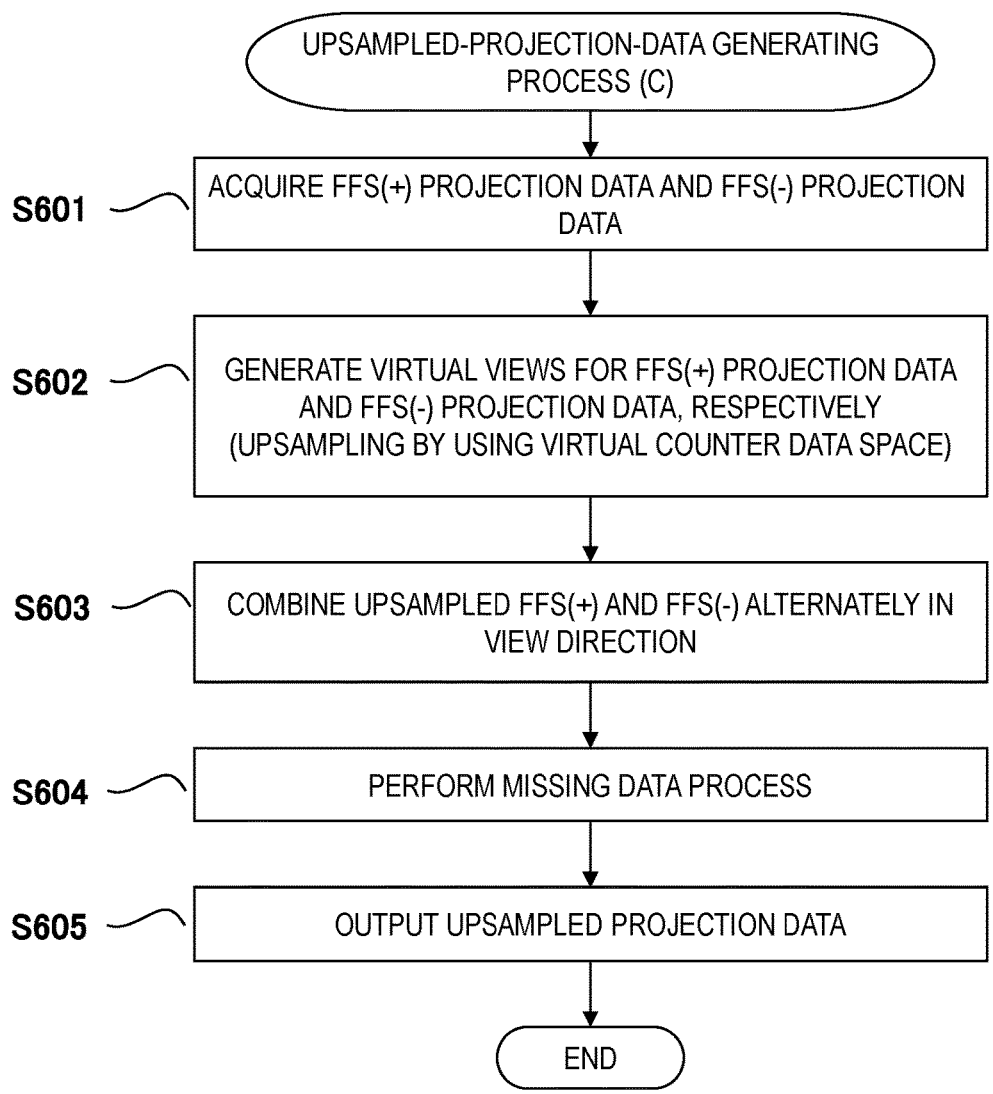
FIG. 16 is a flowchart illustrating flow of an upsampled-projection-data generating process (C).
Figure 18:
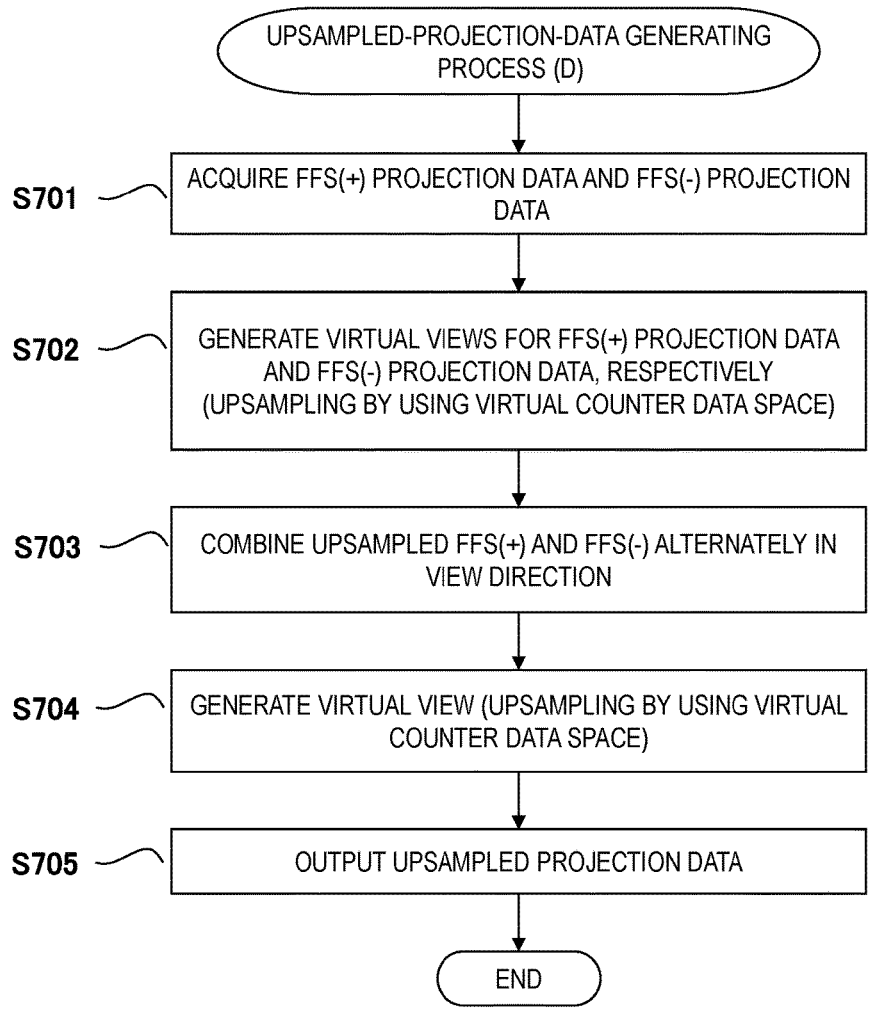
FIG. 18 is a flowchart illustrating flow of an upsampled-projection-data generating process (D).

Similar to the first embodiment (FIGS. 3 and 4), it is possible to apply a calculating method (upsampling method) of the virtual view using the virtual counter data space to the virtual view generating processes in Step S403 in FIG. 12, Step S502 in FIG. 14, Step S602 in FIG. 16, Steps S702 and S704 in FIG. 18.

In other words, the upsampled-projection-data generating unit 127A (image calculating device 122A) calculates the projection data of the virtual view by using the approaching projection data in the inserted view (virtual view) in the view direction or the channel direction, data of counter rays (counter data), or approaching projection data in the view direction or the channel direction of the counter data.

(Virtual-View Calculating Method Using Virtual Counter Data Space; Virtual-Counter-Data Generating Process)

It is possible to generate the virtual view in the projection data obtained through scanning performed by one rotation (2π) by using the data of counter rays (hereinafter, with the data of counter rays referred to as the counter data). With reference to FIG. 3, the example in which the virtual view is generated by using the counter data and the number of views is doubled in the projection data obtained through the scanning by one rotation is described.

The image calculating device 122A (projection-data converting unit 126) acquires the helical projection data (the helical FFS(+) projection data and the helical FFS(−) projection data) obtained through the helical scanning or the continuous reciprocating scanning, and converts the acquired data into the normal projection data (the normal FFS(+) projection data and the normal FFS(−) projection data) at the target slice position by using the 180-degree interpolation, the 360-degree interpolation, or the z filter process (refer to FIG. 2). The axial projection data (axial FFS (+) projection data and the axial FFS(−) projection data) is data as illustrated in FIG. 3(*a*).

The image calculating device 122A (upsampled-projection-data generating unit 127A) performs the process of inserting the virtual views in the projection data (normal FFS(+) projection data and normal FFS(−) projection data) obtained after the conversion.

It is possible to apply the virtual counter data generating process described in the first embodiment on the FFS(+) projection data and the FFS(−) projection data.

In other words, Ray31 and Ray32 face each other in the projection data (the normal FFS(+) projection data and the normal FFS(−) projection data) obtained by one rotation illustrated in FIG. 3(*a*).

In other words, the rays have the same X-ray irradiation path. The items of counter data of the point A1 and the point A2 on Ray31 correspond to the point B1 and the point B2 on Ray32, respectively. The point B1 and the point B2 are items of data of adjacent channels on the same view view (2γm+π) as illustrated in FIG. 3(*a*). The relationship between the point A1 and the point B1 on the projection data can be expressed in Expression (1) described above by using the function R(γ, θ) using parameters obtained when γ represents the channel direction and θ represents the view direction.

In addition, a relationship between the channel and the view at the point A1 and the point B1 can be expressed in the following expressions (2) and (3).

In this manner, the point A1A2 in a virtual view 41 between the point A1 and the point A2 is found to correspond to a point B1B2 as the virtual channel inserted between the point B1 and the point B2 on the view view (2γm+α). It is possible to calculate, from the following expressions (4) and (5), a value of the virtual counter data point A1A2 on the counter data (Ray31) with respect to the virtual channel (point B1B2) on Ray32 (view view (2γm+π)).

In the same procedure, as illustrated in FIG. 3(*b*), a virtual counter data point C1C2 adjacent to the point A1A2 by one pixel in the virtual view 41 is calculated. The virtual counter data space is generated while iterating the same procedure. As illustrated in FIG. 3(*c*), a value of a point V41*b* as a channel position of the virtual view 41 is obtained by interpolation of the virtual counter data points A1A2 and C1C2 on the virtual counter data space. Iteration of such an operation is performed, and thus values of the channels of the virtual view 41 are calculated (points represented by double circles in FIG. 3(*c*)). Regarding other virtual views 42, 43, and the like, similarly, it is possible to calculate channel data by using the virtual counter data.

In the generating method (upsampling method) of the virtual views using the virtual counter data space, channel data of the virtual view is calculated on the basis of the virtual counter data (actual data) having the most approximating living body information (measurement data obtained by transmission through the object) with respect to the channel data (points represented by double circles) which is to be estimated. The virtual counter data having the most approximating living body information is the rays which have closest transmission paths in the measured rays and the rays which are incident from opposite directions. The rays are selectively acquired, virtual rays, which are estimated from the selected rays, are calculated, and the virtual view is generated. In such a technique, it is possible to upsample only the number of views with the number of channels remaining as is. In a case of doubling the sampling, the channel data of the virtual view is obtained by using an average value of the counter data from two points; however, in a case where the sampling is performed N times, the channel data may be obtained through the linear interpolation between two points or non-linear interpolation. In addition, in such a method, it is possible to simultaneously perform the upsampling also in the channel direction.

The generation method of the virtual view is not limited to the upsampling method using the counter data described above. The two-point interpolation mat be performed by interpolation between simply adjacent views as illustrated in FIG. 4(*a*), or the four-point interpolation may be performed by interpolation using data of adjacent views and adjacent channels as illustrated in FIG. 4(*b*), or the total variation (TV) method may be used as illustrated in FIG. 4(*c*).

In addition, the number of views of the upsampling projection data may be any of the number of views including a decimal number such as 1.5 times the actual data or the like. For example, in a case where the number of views partially increases in the view direction, decimal multiple of the number of views is obtained. A cross section of an object 2 has a shape that approximates to an ellipse, as illustrated in FIG. 20(*a*). Therefore, as illustrated in FIG. 20(*b*), a partial increase in the number of views is achieved, such as the large number of views may be densely provided in the view corresponding to a longitudinal diameter of the ellipse, and thus it is possible to generate the upsampled projection data 518 by decimal multiple.

Figure 22:
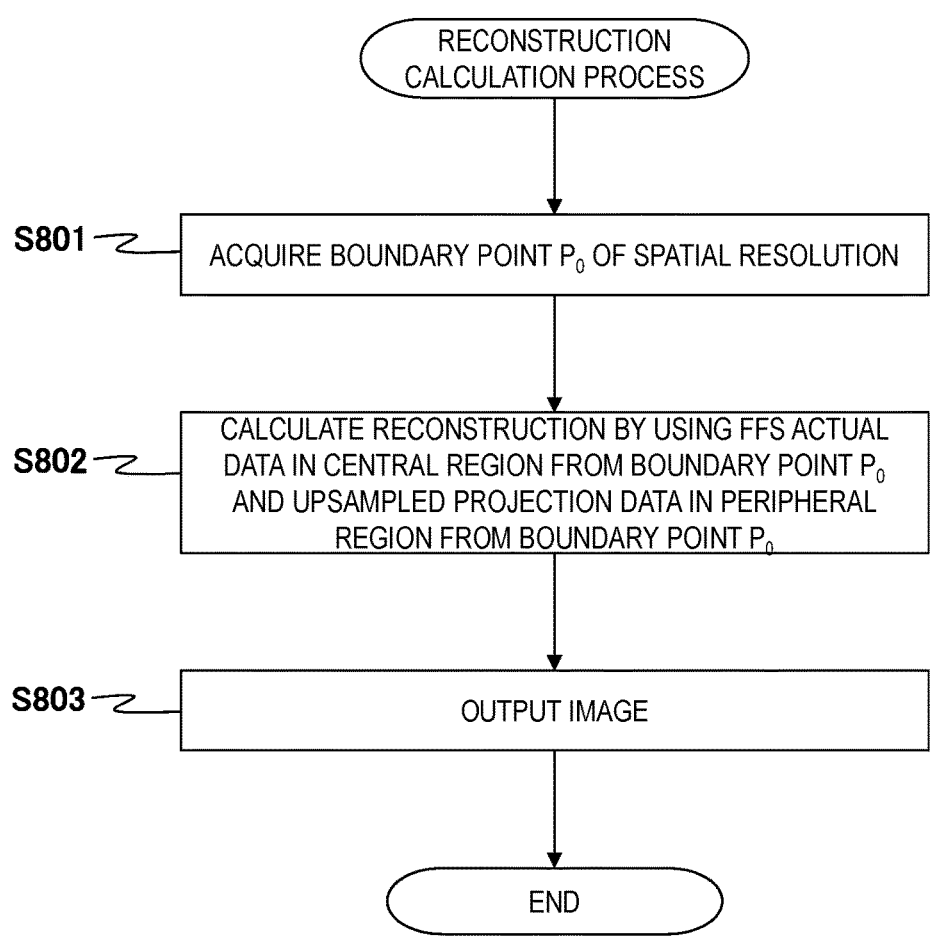
FIG. 22 is a flowchart illustrating flow of a reconstruction calculating process.

Next, the reconstruction calculation process in Step S304 in FIG. 11 is described with reference to FIGS. 21 to 23.

As described above, the spatial resolution of the image which is reconstructed by using the FFS projection data is high in the central region of the image, compared to a case where the FFS projection data is not used, and is lower than in a case where the projection data without FFS is used at a position close to the periphery (refer to FIG. 21).

FIG. 21(*b*) illustrates a graph 606 showing a relationship between a distance from the center O and the spatial resolution in the tomogram 601 in FIG. 21(*a*). In a case of using the FFS projection data, in a region (hereinafter, referred to as a central region 604) on the inner side of a boundary 605 at a distance $P_0$ from the image center O, (an index value representing) the spatial resolution is high, compared to a case of using the FFS (NO) projection data. On the other hand, in a region (hereinafter, referred to as a peripheral region 603) on the inner side from a boundary point $P_0$ (boundary 605 illustrated in FIG. 21(*a*)), (an index value representing) the spatial resolution is low, compared to a case of using the FFS(NO) projection data.

The image reconstruction is performed on the data of the central region 604 having already sufficient spatial resolution by using the FFS projection data (actual data) on which the upsampling is not performed. In the peripheral region 603, the image reconstruction is performed by using the projection data upsampled through the generation of the virtual view, and thereby the spatial resolution of the peripheral region 603 improves.

In this manner, in the central region 604, it is possible to improve the spatial resolution while an adverse effect due to the generation of the data is prevented. In addition, in the peripheral region 603, it is possible to increase the number of views without a decrease in the rotating speed through generating of the virtual view, and thereby it is possible to improve the spatial resolution.

A procedure of the reconstruction calculation process is described with reference to a flowchart in FIG. 22.

First, the image-reconstruction calculating unit 128A acquires the boundary point $P_0$ of the spatial resolution (Step S801). The boundary point $P_0$ is positioned at a distance from the scanning center to a position at which the spatial resolution obtained by the FFS projection data and the spatial resolution obtained by the FFS (NO) projection data are reversed. The boundary point $P_0$ is obtained by experimental data in advance, and is stored in the storage device 123 or the like.

A modulation transfer function (MTF) is used as an evaluation index value of the spatial resolution. For example, the boundary point $P_0$ described above is obtained for each different spatial resolution index value such as MTF 50%, 10%, 2% or the like, and selected by an operator. Since the image quality needs to be different depending on the examination and diagnostic purpose, it is desirable to select the spatial resolution depending on a balance between image quality (noise or the like)

Otherwise, another boundary point may be obtained as the center of gravity from the boundary point $P_0$ obtained by the spatial resolution index values such as MTF 50%, 10%, 2% or the like.

The image-reconstruction calculating unit 128A performs the reconstruction calculation by using the actual data of the FFS projection data in the central region 604 on the inner side from the boundary point $P_0$, and using the upsampled projection data obtained with the FFS projection data subjected to the upsampling in the peripheral region 603 on the outer side from the boundary point $P_0$ (Step S802).

The upsampled projection data used in the peripheral region 603 may be any upsampled projection data generated by any method of the upsampled-projection-data generating processes (A) to (D). In other words, the upsampled projection data 505 generated in the upsampled-projection-data generating process (A) illustrated in FIGS. 12 and 13 may be used as illustrated in FIG. 23(a), the upsampled projection data 513 generated in the upsampled-projection-data generating process (B) illustrated in FIGS. 14 and 15 may be used as illustrated in FIG. 23(b), the upsampled projection data 515 generated in the upsampled-projection-data generating process (C) illustrated in FIGS. 16 and 17 may be used as illustrated in FIG. 23(c), the upsampled projection data 516 generated in the upsampled-projection-data generating process (D) illustrated in FIGS. 18 and 19 may be used as illustrated in FIG. 23(d).

In addition, as the generating method of the virtual view, regarding any of the upsampled projection data 505, 513, 515, and 516, an upsampling method of using the virtual counter data space as described above may be employed, the interpolation between adjacent two points in the view direction may be used, or the interpolation between adjacent four points in the view direction and the channel direction may be used, or the interpolation or the like using the TV method or the like may be used.

In the reconstruction calculation, the FFS projection data (data before the upsampling) after conversion into the normal projection data and the upsampled projection data are combined on the projection data, then, the reconstruction of the image such as the back projection process may be performed, or an image may be generated by combining a portion corresponding to the central region 604 of the image reconstructed by using the actual data (data before the upsampling) of the FFS projection data and a portion corresponding to the peripheral region 603 of the image reconstructed by using the upsampled projection data.

The image-reconstruction calculating unit 128A outputs the image generated in the process in Step S802 (Step S803). The output destination is, for example, the storage device 123 or the display device 125.

As described above, the X-ray CT apparatus 1A of the second embodiment converts the focus shifted projection data (helical FFS projection data) obtained by causing the X-ray focus position to shift in the X-ray tube device 101A, and performing helical scanning, into the normal projection data, and performs the upsampling in the view direction. In the reconstruction calculation process of the image, the image is reconstructed by using the actual data (normal FFS projection data) of the FFS projection data in the central region 604 closer to the center of the scanning than to the predetermined boundary point $P_0$, and by using the upsampled projection data in the peripheral region 603 which is apart from the scanning center by the boundary point $P_0$.

Since the data upsampled by the virtual view is used in a peripheral portion out of the effective field of view, there is no need to perform scanning by decreasing the rotating speed such that the number of views increases. Hence, it is possible to improve the spatial resolution of the peripheral portion regardless of the limit of the rotation speed due to the hardware limit, and it is possible to improve the spatial resolution of the entire effective field of view. Such a method is preferable to be used in the scanning of the portion having motion.

Third Embodiment

Next, the third embodiment of the present invention will be described with reference to FIGS. 24 to 26.

The X-ray CT apparatus 1A of the third embodiment performs a joining process in the reconstruction calculation process of the second embodiment such that the spatial resolution is smoothly continuous on the boundary point $P_0$.

In the joining process, as illustrated in FIG. 24, both of the image reconstructed by the FFS actual projection data and the image reconstructed in response to the upsampled projection data are combined with a predetermined ratio in a predetermined range of a region (hereinafter, referred to as a boundary region Q) including the boundary point $P_0$. In a central region 604a close to the central portion from the boundary region Q, similar to the second embodiment, 100% of the image reconstructed by the actual data of the FFS projection data is used. In a peripheral region 603a on the outer side from the boundary region Q, similar to the second embodiment, 100% of the image reconstructed by the upsampled projection data is used.

In other words, the image reconstructed in response to the FFS projection data and the image reconstructed by the upsampled projection data are combined with each other by changing weights, depending on a distance from the center.

Figure 25:
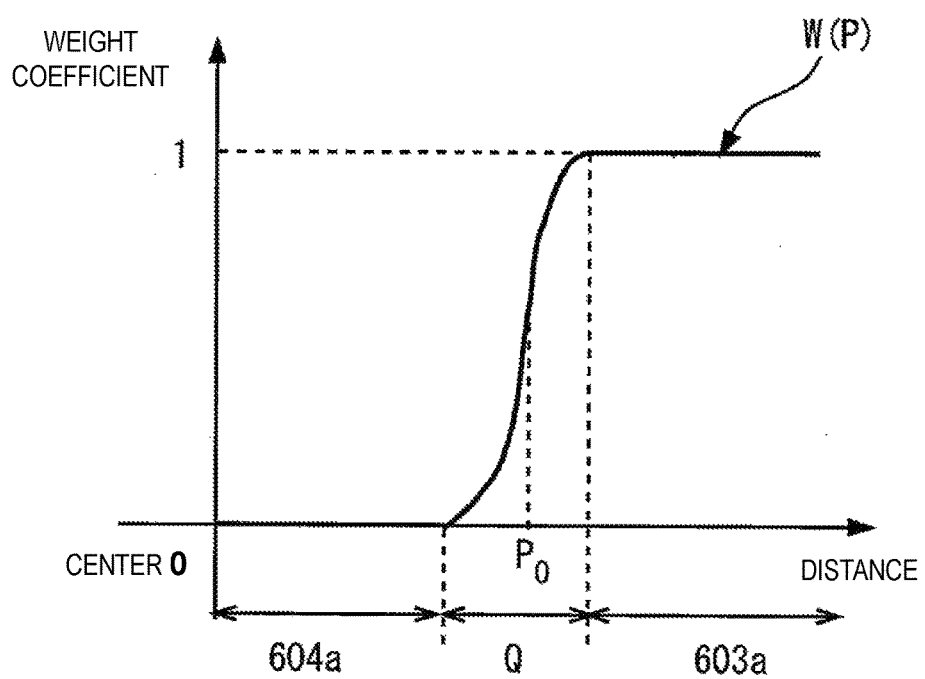
FIG. 25 illustrates an example of a weight coefficient in the reconstruction calculating process of the third embodiment.
Figure 26:
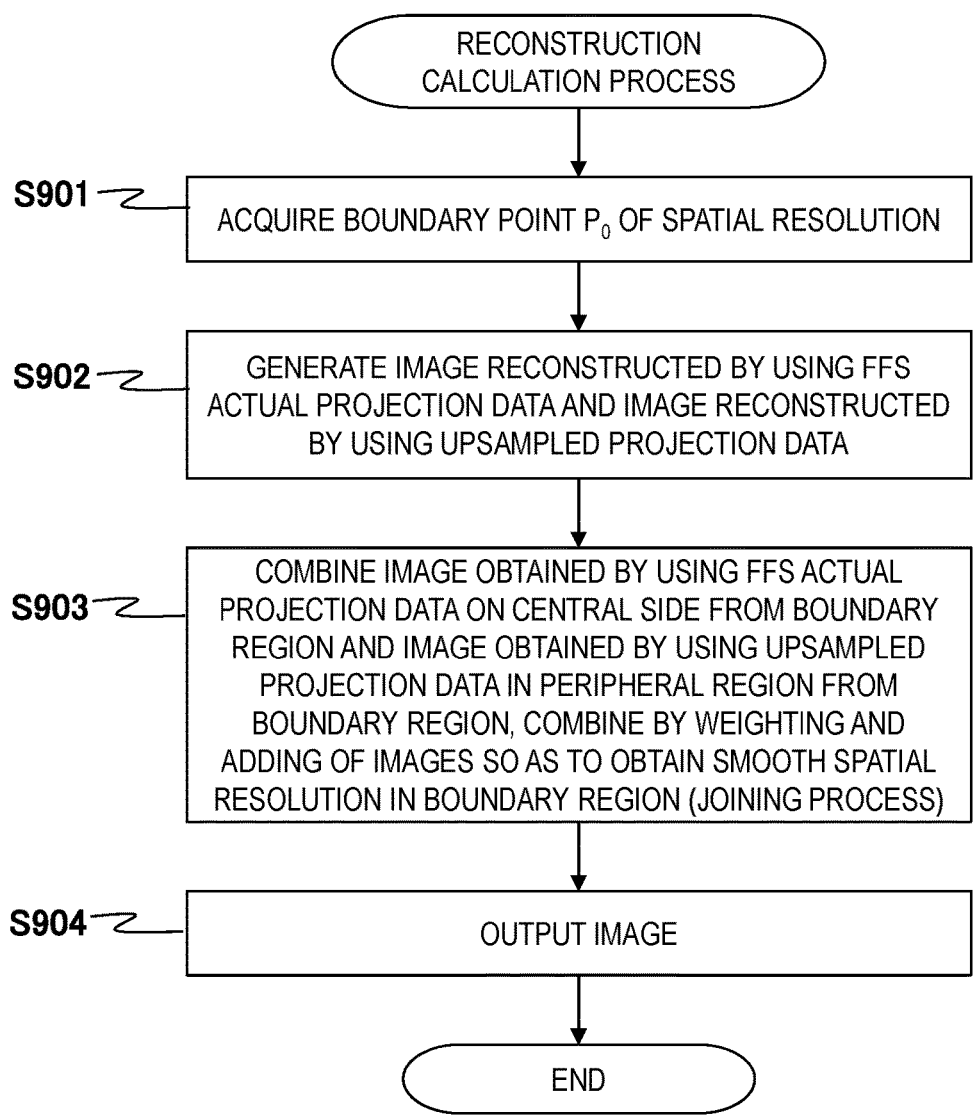
FIG. 26 is a flowchart illustrating flow of the reconstruction calculating process of the third embodiment.

FIG. 25 illustrates a graph showing the weight coefficient used for a reconstructed image by the upsampled projection data. As illustrated in FIG. 25, the weight coefficient W(P) changes depending on a distance P from the center o. The weight coefficient is "0" in the central region 604a, a smoothly rising curve in a boundary region Q, and "1" in the peripheral region 603a. The weight coefficient used in the reconstructed image changes depending on a distance from the center O in response to the FFS projection data (normal FFS projection data); however, the weight coefficient W(P) illustrated in FIG. 25 reversely is "1" in the central region 604a, a smooth downward curve in the boundary region Q, and "0" in the peripheral region 603a.

A range of the boundary region Q may be arbitrarily set, and may change depending on desirable spatial resolution in a desirable region.

In addition, the weight coefficient in an example in FIG. 25 is represented by a smooth curve depending on a distance P from the image center; however, the weight coefficient is not limited thereto, and may be represented by a straight line or a polygonal line.

In addition, also in the third embodiment, as illustrated in FIGS. 24(a) to 24(d), the upsampled projection data used in the peripheral region 603a and the boundary region Q may use the upsampled projection data generated through any method of the upsampled-projection-data generating processes (A) to (D).

Figure 13:
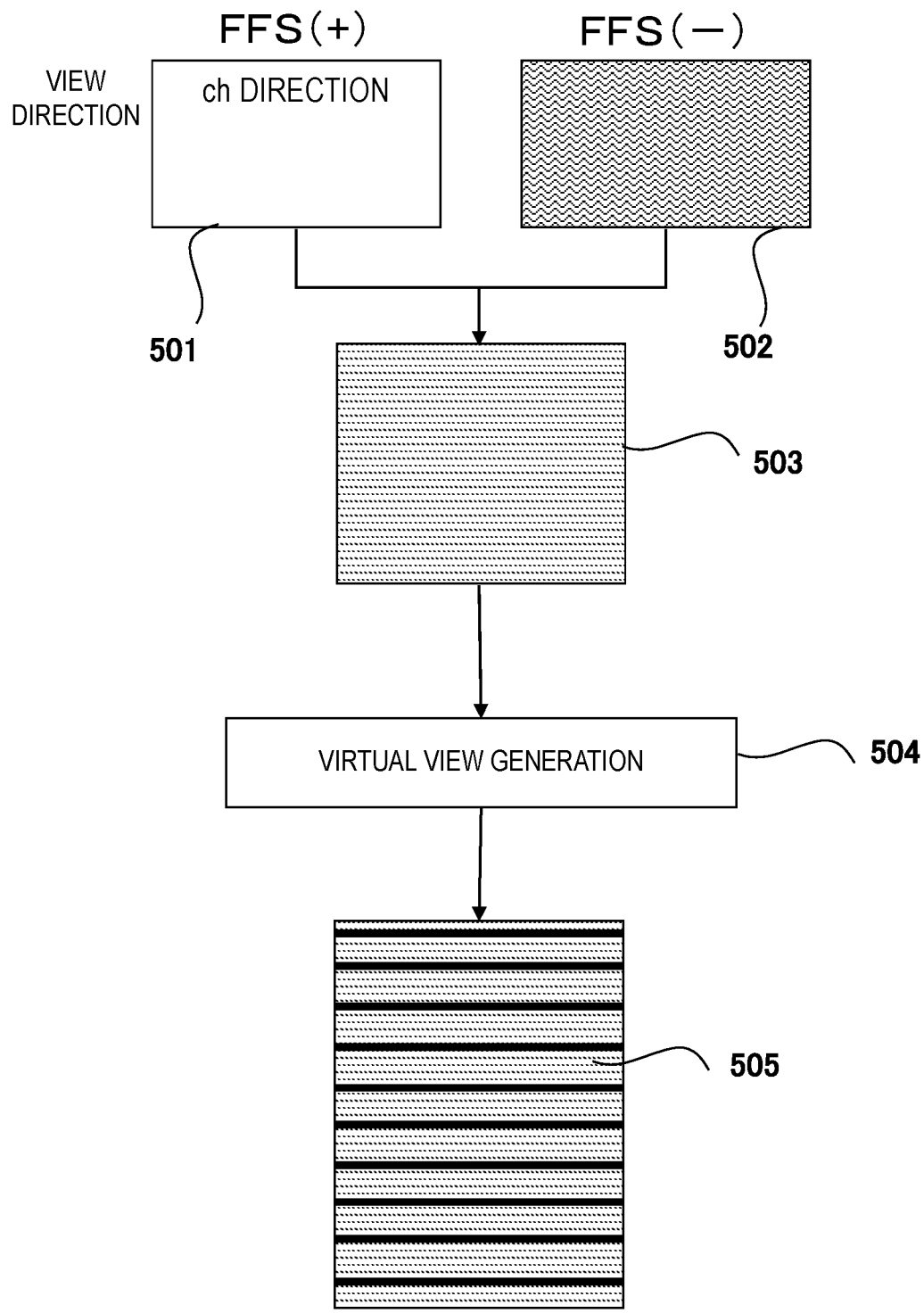
FIG. 13 is a conceptual diagram illustrating a procedure of the upsampled-projection-data generating process (A).
Figure 15:
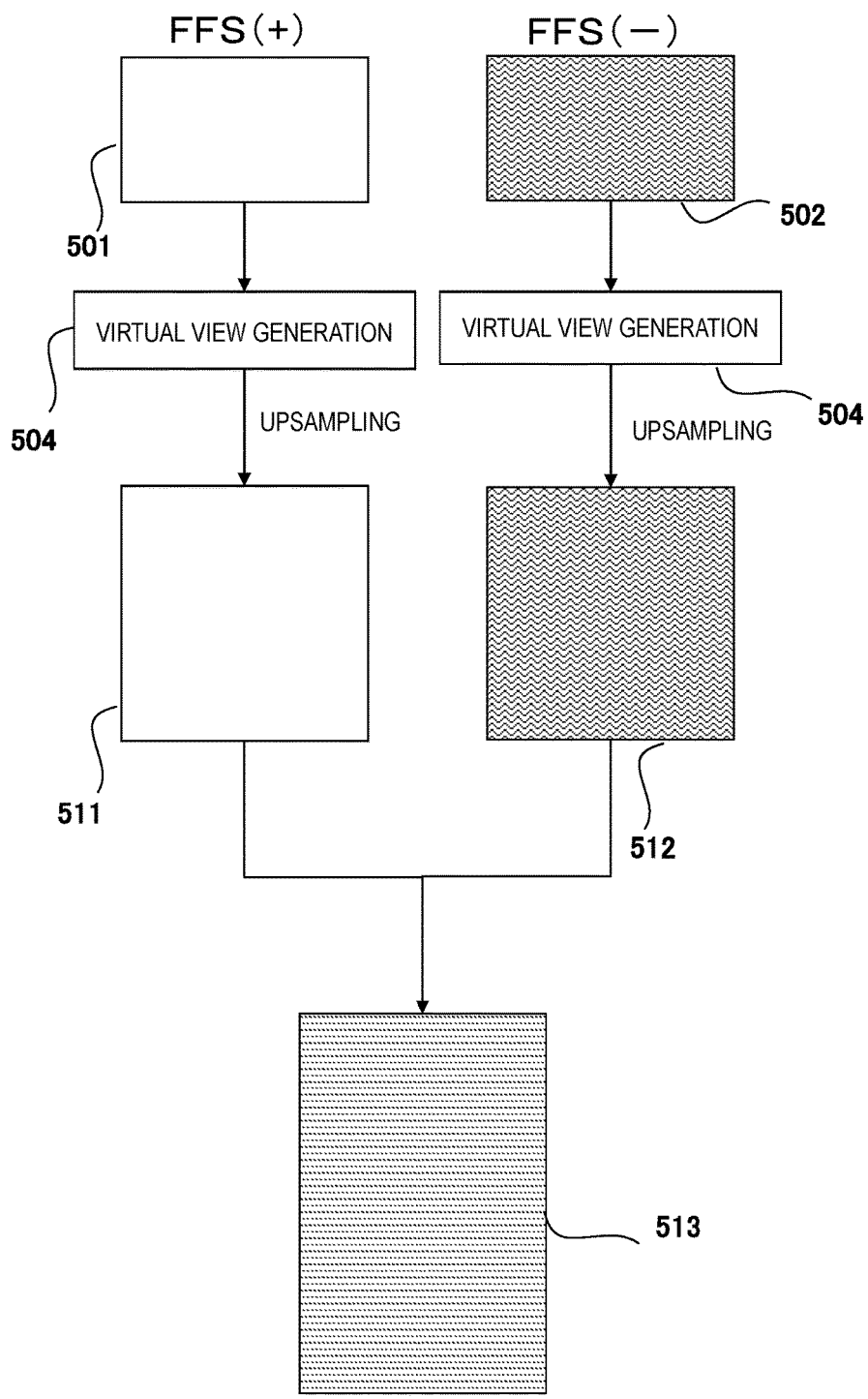
FIG. 15 is a conceptual diagram illustrating a procedure of the upsampled-projection-data generating process (B).
Figure 17:
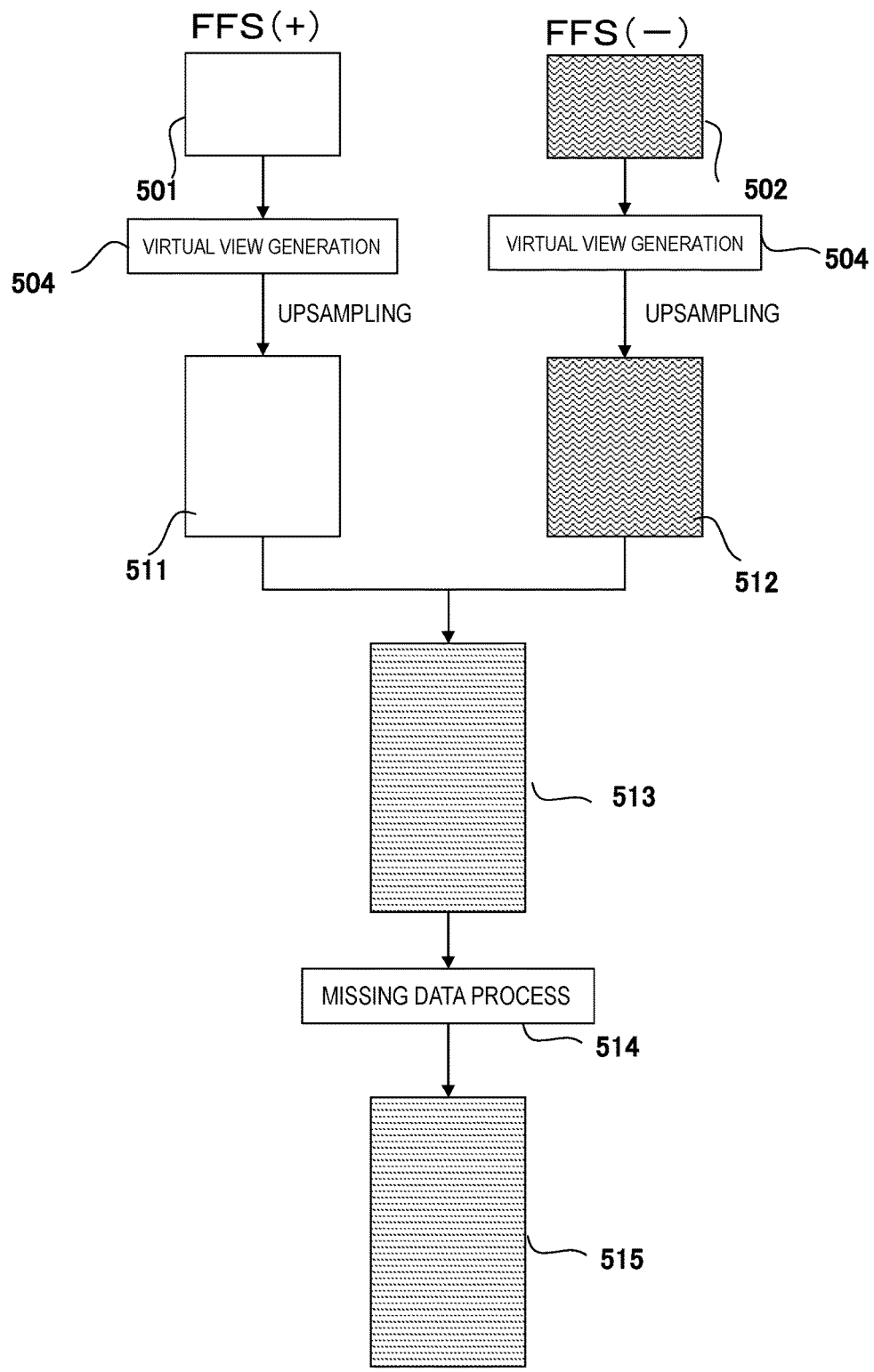
FIG. 17 is a conceptual diagram illustrating a procedure of the upsampled-projection-data generating process (C).
Figure 19:
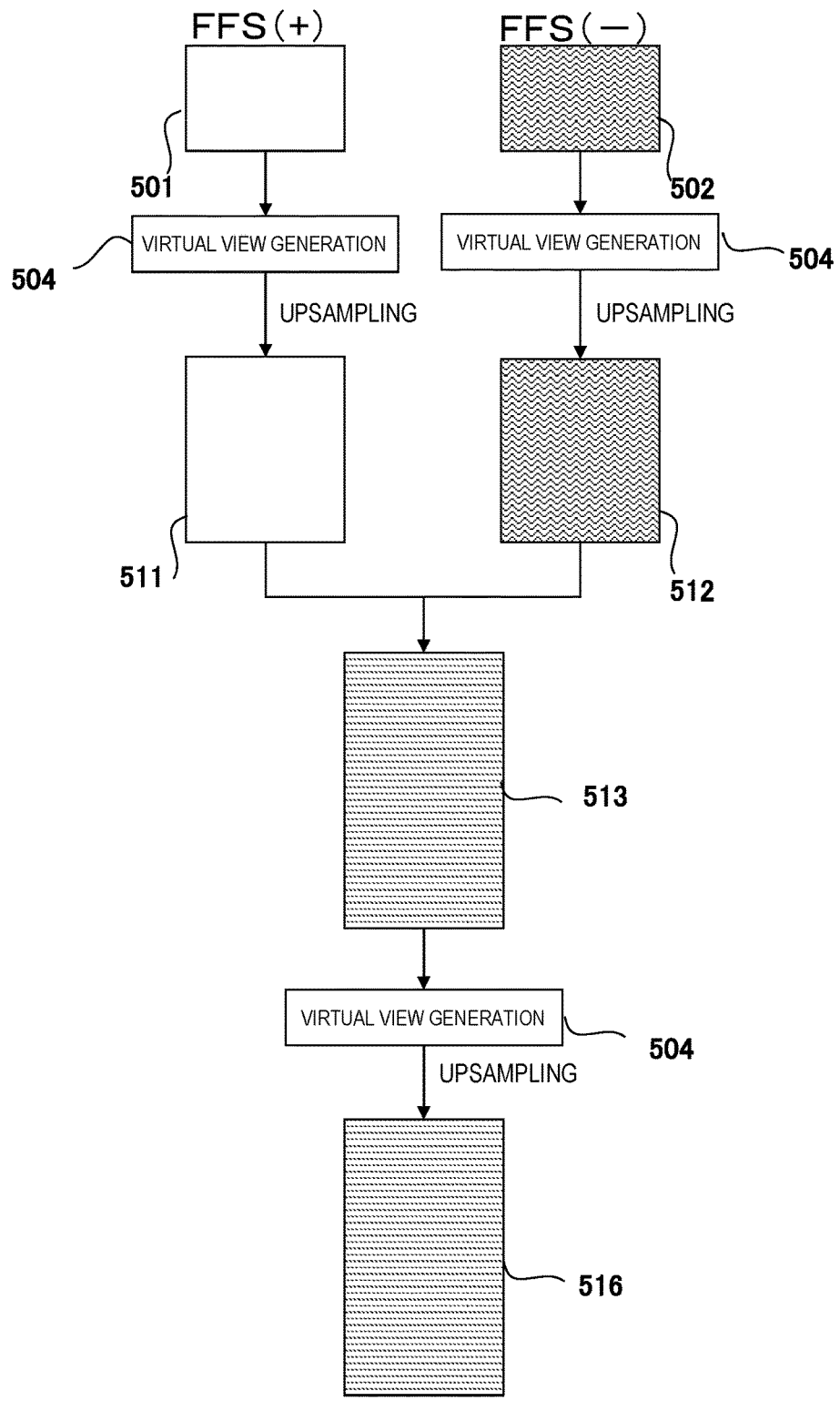
FIG. 19 is a conceptual diagram illustrating a procedure of the upsampled-projection-data generating process (D).

In other words, the upsampled projection data 505 generated in the upsampled-projection-data generating process (A) illustrated in FIGS. 12 and 13 may be used as illustrated in FIG. 24(a), the upsampled projection data 513 generated in the upsampled-projection-data generating process (B) illustrated in FIGS. 14 and 15 may be used as illustrated in FIG. 24(b), the upsampled projection data 515 generated in the upsampled-projection-data generating process (C) illustrated in FIGS. 16 and 17 may be used as illustrated in FIG. 24(c), the upsampled projection data 516 generated in the upsampled-projection-data generating process (D) illustrated in FIGS. 18 and 19 may be used as illustrated in FIG. 24(d).

In addition, as the calculation method of the virtual view, regarding any of the upsampled projection data 505, 513, 515, and 516, the interpolation (FIG. 4(a)) between adjacent two points in the view direction described above may be used, the interpolation (FIG. 4(b)) between adjacent four points in the view direction and the channel direction may be used, the interpolation or estimation (FIG. 4(c)) using the TV method or the like may be used, or the calculation by using the virtual counter data space may be used (FIG. 3).

In addition, the number of views of the upsampling projection data is not limited to doubling the actual data, and may further increase more than double. In addition, the number of views in the view direction may partially increase, or may contain any number of views including a number smaller than 1.5 times.

Flow of the reconstruction calculation processes of the third embodiment is described with reference to FIG. 26.

First, the image-reconstruction calculating unit 128A acquires the boundary point $P_0$ of the spatial resolution (Step S901). Acquisition of the boundary point $P_0$ is the same as that in the second embodiment (Steps S801 in FIG. 22).

The image-reconstruction calculating unit 128A generates an image reconstructed by using the actual data (normal FFS projection data) of the FFS projection data, and an image reconstructed by using the upsampled projection data obtained by upsampling the FFS projection data (Step S902).

In addition, the image-reconstruction calculating unit 128A generates a composite image by using the image reconstructed with the actual data of the FFS projection data in the central region 604a on the central side from the boundary region Q containing the boundary point $P_0$, and using the image reconstructed by using the upsampled projection data in the peripheral region 603a on the outer side from the boundary region Q. The images reconstructed in Step S902 are weighted and added such that the continuous spatial resolution is obtained in the boundary region Q (Step S903). As described above, the weighted method is performed by applying the weight coefficient having the shape illustrated in FIG. 25 to the image generated in response to the upsampled projection data, applying the weight coefficient having a shape reversed from the graph illustrated in FIG. 25 to the image generated in response to the FFS actual projection data (normal projection data), and then the images are combined.

The image-reconstruction calculating unit 128A outputs the image generated in the process in Step S903 (Step S904). The output destination is, for example, the storage device 123 or the display device 125.

As described above, the X-ray CT apparatus 1A of the third embodiment combines, in the reconstruction calculation process of the image, the images reconstructed by using the actual data (normal FFS projection data) of the FFS projection data in the central region 604a close to the center of the image, and by using the upsampled projection data in the peripheral region 603a on the peripheral side from the boundary point $P_0$. Further, in the predetermined boundary region Q, the images described above are weighted and added so as to have smooth continuous spatial resolution.

In this manner, it is possible to further obtain the image having the smooth continuous spatial resolution in the boundary region Q, in addition to the effects of the second embodiment.

In the reconstruction calculation process, the reconstructed images are weighted and added while the images are combined; however, the upsampled projection data and the actual data (normal FFS projection data) of the FFS projection data may be combined on the projection data, and then the combined projection data may be reconstructed. In this case, in the portion corresponding to the boundary region Q, the projection data generated by weighting and adding the upsampled projection data and the actual data (normal FFS projection data) of the FFS projection data is used.

Fourth Embodiment

Next, the fourth embodiment of the present invention will be described with reference to FIGS. 27 and 28.

In the X-ray CT apparatus 1A of the fourth embodiment, the weight may be changed over the entire image, and the image generated by using the actual data (normal projection data) of the FFS projection data, and the image generated by using the upsampled projection data may be combined.

Figure 27:
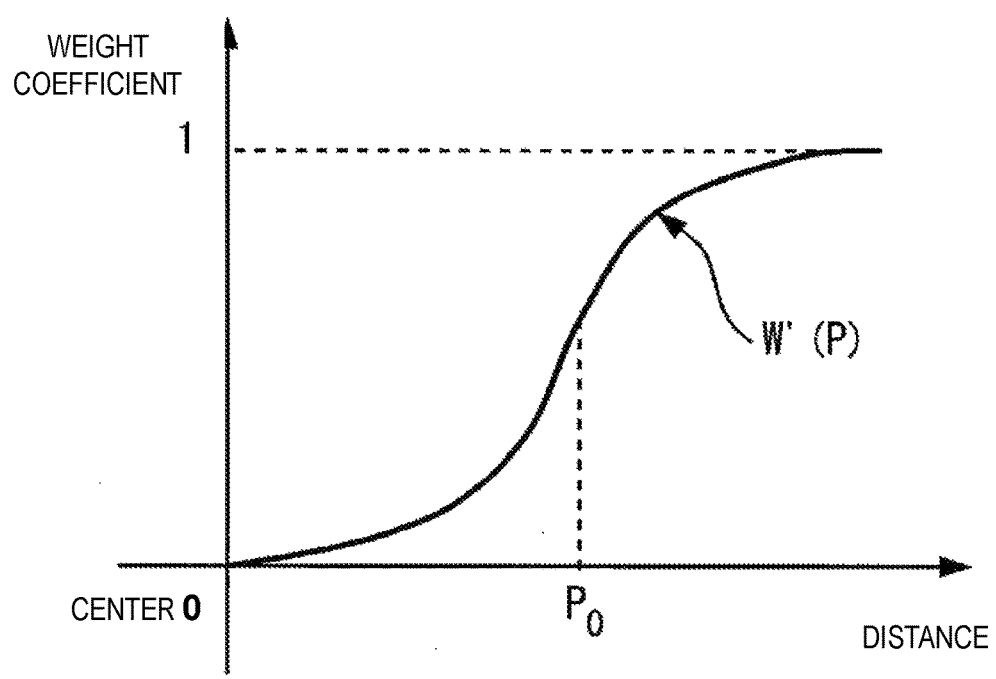
FIG. 27 illustrates an example of a weight coefficient in the reconstruction calculating process of the fourth embodiment.
Figure 28:
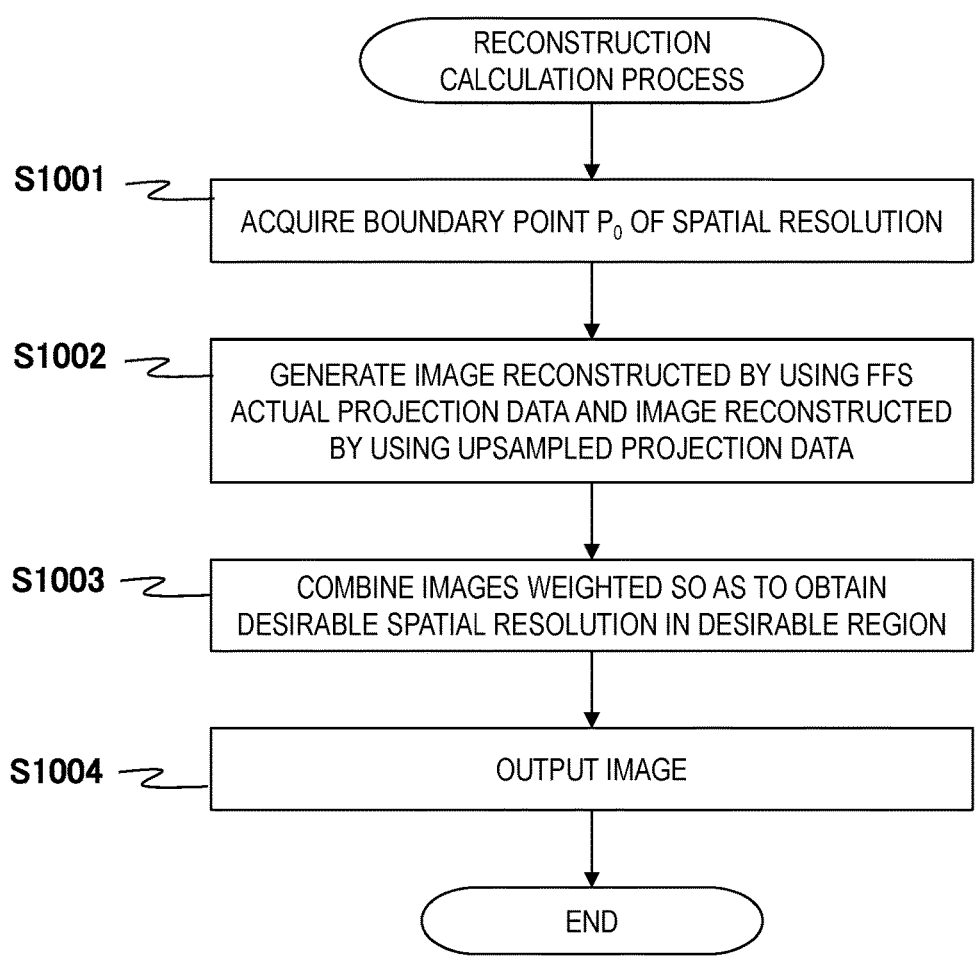
FIG. 28 is a flowchart illustrating flow of the reconstruction calculating process of the fourth embodiment.

FIG. 27 illustrates a graph showing the weight coefficient W' (P) applied to the reconstructed image generated by using the upsampled projection data according to the fourth embodiment. In the graph, the weight coefficient smoothly increases from "0" in a region close to the center, and is "1" in an end portion of the peripheral region. In other words, the weight coefficient has a shape changing depending on a distance from the center O even in a region other than the boundary region Q. As described above, the graph of the weight coefficient may have any shape, or the weight coefficient is caused to change such that desirable spatial resolution is obtained in a desirable region even in a region other than the boundary region Q.

Contrary to FIG. 27, the weight coefficient applied to the reconstructed image generated by using the FFS projection data (normal FFS projection data) smoothly decreases from. "1" in the region closer to the center and becomes "0" in the end portion of the peripheral region.

In addition, the weight coefficient W' (P) in an example in FIG. 27 is represented by a smooth curve depending on the distance P from the image center; however, the weight coefficient is not limited thereto, and may be represented by a straight line.

The flow of the reconstruction calculation processes of the fourth embodiment is described with reference to FIG. 28.

First, the image-reconstruction calculating unit 128A acquires the boundary point $P_0$ of the spatial resolution (Step S1001). Acquisition of the boundary point $P_0$ is the same as that in the second embodiment (Step S801 in FIG. 22).

Next, the image-reconstruction calculating unit 128A generates an image reconstructed by using the actual data (normal FFS projection data) of the FFS projection data, and an image reconstructed by using the upsampled projection data obtained by upsampling the normal FFS projection data (Step S1002).

The upsampled projection data used may be any upsampled projection data generated by any method of the upsampled-projection-data generating processes (A) to (D).

Next, the image-reconstruction calculating unit 128A adds the weight coefficient having a desirable shape to the images (Step S1003). The weighting means that combination is performed with an appropriate ratio such that desirable spatial resolution is obtained in a desirable region, when the image reconstructed by using the actual data (normal FFS projection data) of the FFS projection data and the images reconstructed by using the upsampled projection data obtained by upsampling the normal FFS projection data are combined.

The image-reconstruction calculating unit 128A outputs the image generated in the process in Step S1003 (Step S804). The output destination is, for example, the storage device 123 or the display device 125.

As described above, the X-ray CT apparatus 1A of the fourth embodiment combines, in the reconstruction calculation process of the image, the images reconstructed by using the actual data (normal projection data) of the FFS projection data, and the image reconstructed by using the upsampled projection data, using the weight coefficient changing depending on the distance from the scanning center.

In this manner, it is possible to further obtain the image having the desirable spatial resolution in the desirable region of the image, in addition to the effects of the second embodiment. In addition, the weight of the actual data increases, and thereby it is possible to obtain an image having high reliability in the desirable region.

Fifth Embodiment

Figure 30:
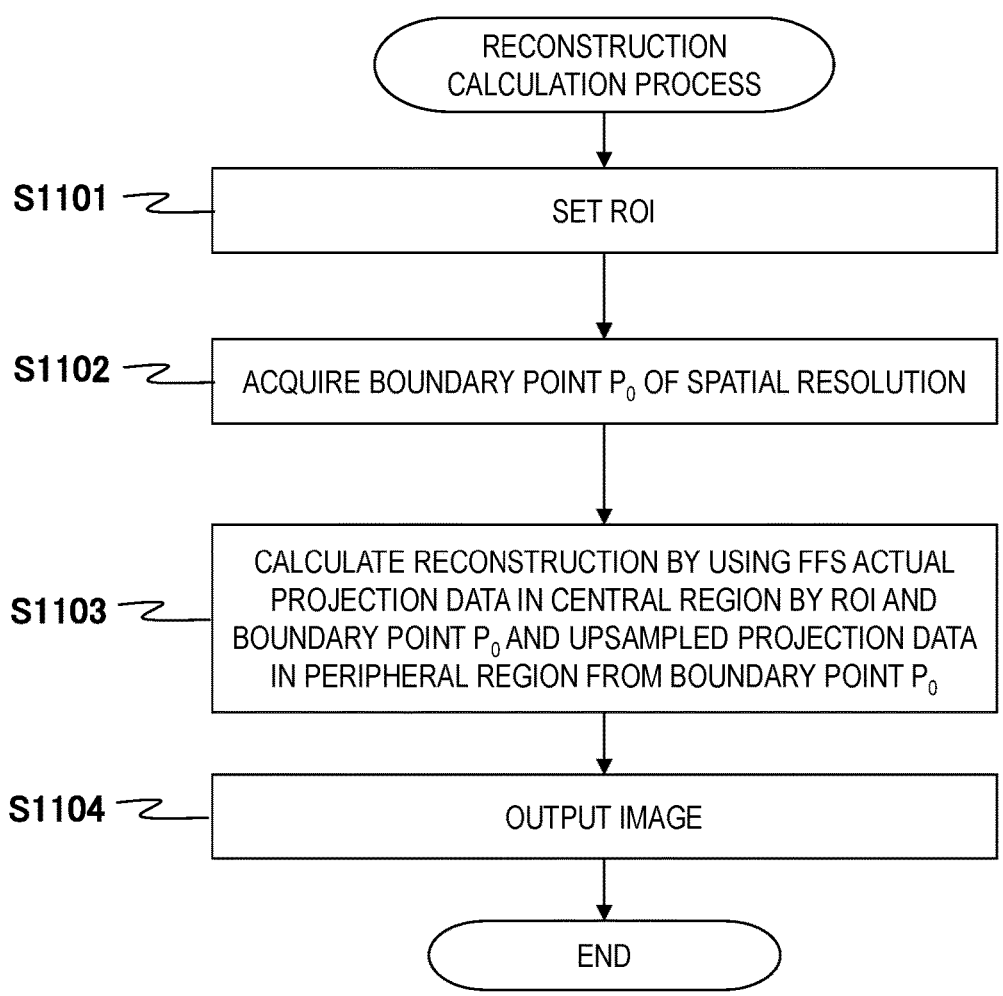
FIG. 30 is a flowchart illustrating flow of the reconstruction calculating process of the fifth embodiment.

Next, the fifth embodiment of the present invention is described with reference to FIGS. 29 to 30.

In the fifth embodiment, as illustrated in FIG. 29, the actual data 503 of the FFS projection data is applied to a region of interest (ROI) 7 set by the operator and the central region 604. In addition, the upsampled projection data 505 is applied to the peripheral region 603. In a case where the ROI 7 is the peripheral region 603, the actual data 503 of the FFS projection data is applied in the range of the ROI 7.

The flow of the reconstruction calculation processes of the fifth embodiment is described with reference to FIG. 30.

First, the system control device 124 sets the region of interest (ROI) 7 (Step S1101). The setting of the ROI 7 is performed by the operator via the input device 121. Next, the image-reconstruction calculating unit 128A acquires the boundary point $P_0$ of the spatial resolution (Step S1102). Acquisition of the boundary point $P_0$ is the same as that in the second embodiment (Steps S801 in FIG. 22).

Next, the image-reconstruction calculating unit 128A reconstructs an image by using the actual data (normal FFS projection data) of the FFS projection data in the central region 604 and the ROI 7 set in Step S1101, and an image by using the upsampled projection data by the virtual views in the peripheral region 603 except for the ROI 7 (Step S1103).

The upsampled projection data used may be any upsampled projection data generated by any method of the upsampled-projection-data generating processes (A) to (D).

The image-reconstruction calculating unit 128A outputs the image generated in the process in Step S1103 (Step S1104). The output destination is, for example, the storage device 123 or the display device 125.

As described above, the X-ray CT apparatus 1A of the fifth embodiment reconstructs an image by using the actual data (normal FFS projection data after conversion into the projection data at the target slice position in a case where the helical scanning is performed) of the FFS projection data in the ROI 7 and the central region 604, and the reliability of the image increases. In addition, the spatial resolution improves by using the upsampled projection data in the peripheral region 603 except for the ROI 7. In this manner, the reliability increases in the ROI 7 as a diagnose target and the central portion of the image, and thus it is possible to obtain an image having high spatial resolution in the peripheral portion.

Also in the fifth embodiment, the joining process as described in the third embodiment may be performed in the boundary region Q, or the image generated by using the FFS projection data and the image generated by using the upsampled projection data may be weighted and added by using the weight coefficient having the desirable shape as described in the fourth embodiment.

Sixth Embodiment

Next, the sixth embodiment of the present invention will be described with reference to FIGS. 31 to 33.

Figure 31:
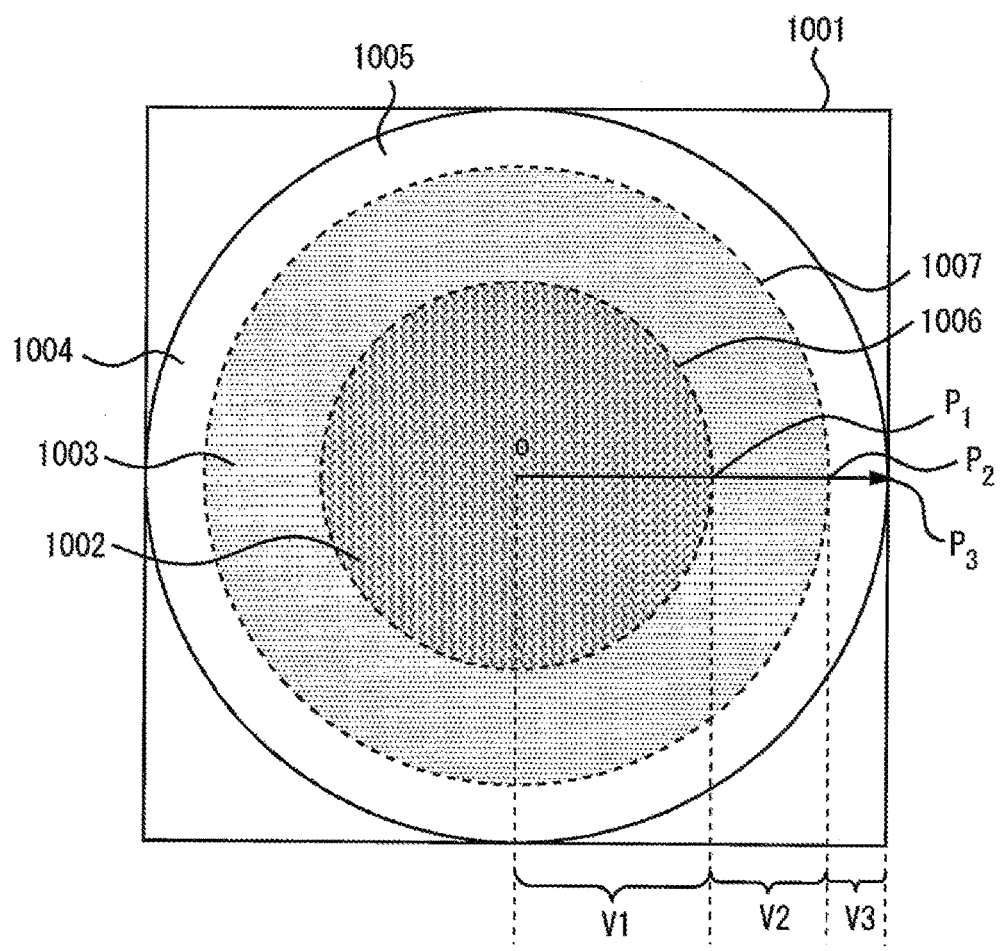
FIG. 31 illustrates a diagram of an example of combining images reconstructed by using upsampled projection data that is different in the number of views depending on a distance from the center of the image, in a reconstruction calculating process of a sixth embodiment.

As illustrated in FIG. 31, in the sixth embodiment, the image-reconstruction calculating unit 128A combines the images reconstructed by using the FFS projection data of the different number of views (the number of upsampling) on a region 1002 from the center O to a distance P1 in the image plane of a reconstructed image 1001, a region 1003 from the distance P1 to a distance P2, and a region 1004 from the distance P2 to a distance P3. For example, the number of views V1 of the actual data of the FFS projection data is used in the region 1002, the FFS projection data subjected to the upsampling to the number of views V2 is used in the region 1003, and the FFS projection data subjected to the upsampling to the number of views V3 is used in the region 1004.

When images before the combination in the regions 1002, 1003, and 1004 are ξ(V1), ξ(V2), and ξ(V3), an image ξ(V) obtained after the combination can be expressed in the following Expression (10).

$$\xi(V)=\xi(V1)+\xi(V2)+\xi(V3) \quad (10)$$

The upsampled projection data may be generated by any method of the upsampled-projection-data generating processes (A) to (D) described in the second embodiment.

Figure 32:
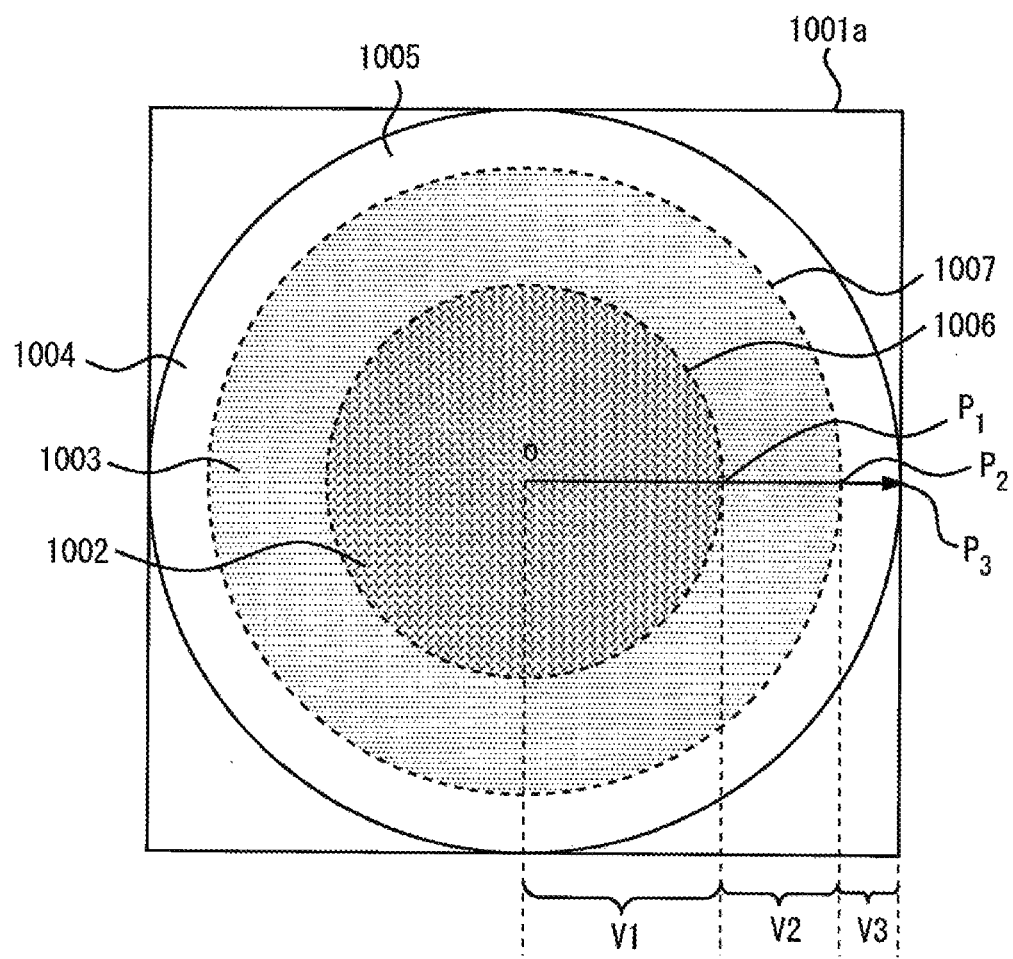
FIG. 32 illustrates a diagram of an example in which images are weighted and combined so as to have a smooth region in the vicinity of a boundary in the example in FIG. 31.

In addition, as illustrated in an image 1001a in FIG. 32, the joining process may be performed so as to obtain the continuous spatial resolution on a boundary between the region 1002 and the region 1003 and a boundary between the region 1003 and the region 1004. The joining process is the same as that of the second embodiment. In other words, on boundaries 1006 and 1007, the combination of the images ξ(V1), ξ(V2), and ξ(V3), which are reconstructed by using the projection data of the number of views, with weight coefficients W(V1), W(V2), and W(V3) such that the spatial resolution continuously and smoothly changes, is performed.

The image ξ(V) obtained after the combination can be expressed by the following Expression (11).

$$\xi(V)=W(V1)\xi(V1)+W(V2)\xi(V2)+W(V3)\xi(V3) \quad (11)$$

Figure 33:
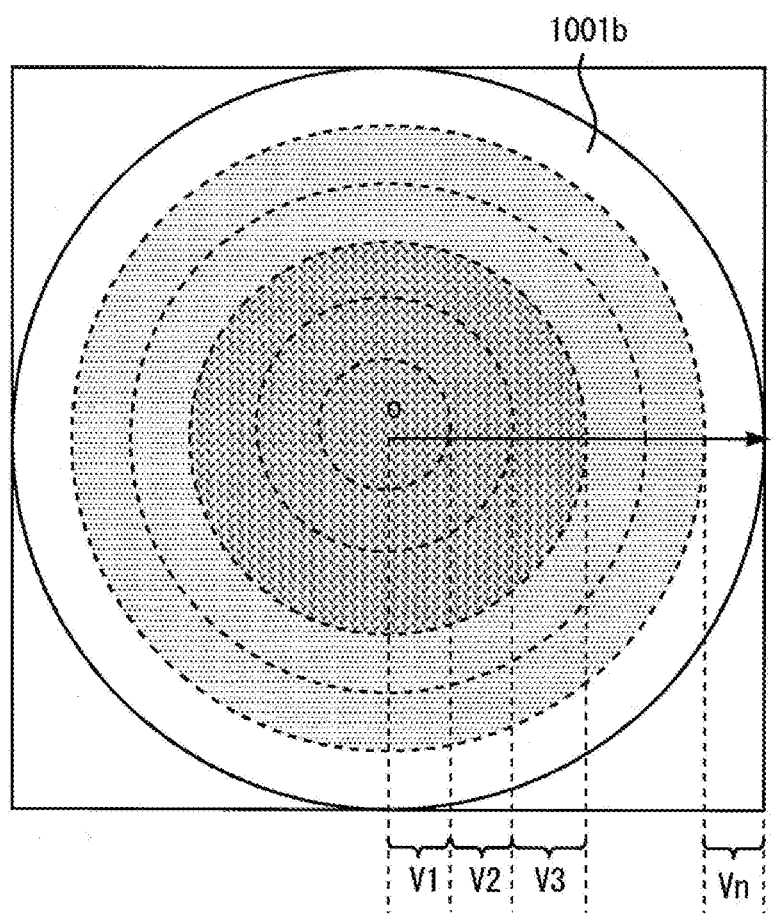
FIG. 33 illustrates a diagram of an example of increasing the number of regions in the example in FIG. 32 to n regions.

In addition, the number of regions in examples illustrated in FIGS. 31 and 33 is three; however, the number of the regions is not limited to three, and it is possible to expand to n regions as shown in an image 1001b in FIG. 33.

The image ξ(V) obtained after the combination can be expressed by the following Expression (12).

$$\xi(V)=W(V1)\xi(V1)+W(V2)\xi(V2)+W(V3)\xi \\ (V3)+\ldots+W(Vn)\xi(Vn) \quad (12)$$

According to the sixth embodiment, it is possible to combine images by using upsampled projection data that is different in the number of views V1 to Vn depending on a distance P from the image center O. Hence, in the peripheral region from the boundary point $P_0$, the number of upsampling is gradually and appropriately increased as a distance from the image center O increases, and thereby it is possible to improve the spatial resolution by a desirable amount. In this manner, it is possible to obtain even spatial resolution over the entire image. In addition, it is possible to generate an image having various degrees of image quality depending on diagnostic purposes such as preferentially improving the spatial resolution in the desirable region.

As described above, the preferred embodiments of the X-ray CT apparatus according to the present invention are described; however the present invention is not limited to the embodiments described above. It is obvious for those skilled in the art to conceive various modification examples or alteration examples within a range of the technical ideas disclosed in this application, and thus it is understood that the examples are included within the technical scope of the present invention.

REFERENCE SIGNS LIST 1, 1A: X-ray CT apparatus
100: scanner gantry
101, 101A: X-ray tube device
102: rotary disk
103: collimator
106: X-ray detector
110, 110A: X-ray control device
120: console
121: input device
122: image calculating device
123: storage device
124: system control device
125: display device
126: projection data converting unit
127, 127A: upsampled-projection-data generating unit
128, 128A: image-reconstruction calculating unit
501: FFS(+) projection data
502: FFS(−) projection data
503: FFS projection data (focal-point shifted projection data)
505, 513, 515, 516, 518: upsampled projection data

The invention claimed is:
1. An X-ray CT apparatus comprising:
an X-ray tube device that performs irradiation with X-rays;
an X-ray detector that is disposed to face the X-ray tube device and detects transmitted X-rays as X-rays transmitted through an object;
a rotary disk on which the X-ray tube device and the X-ray detector are mounted and which rotates around the object;
a scanner gantry on which the rotary disk is mounted;
a couch on which the object is positioned;
a scanning control unit that causes the couch and the scanner gantry to relatively move in a body-axial direction while causing the rotary disk to rotate and collects data of the transmitted X-rays detected by the X-ray detector;
a projection-data converting unit that performs predetermined data processing on the collected data of transmitted X-rays and generates projection data required for reconstruction of a tomogram at a target slice position;
an upsampled-projection-data generating unit that generates virtual counter data containing counter data acquired on substantially coincident X-ray transmission path in the projection data, thereby upsampling the projection data;
a reconstruction calculating unit that reconstructs an image by using upsampled projection data as projection data subjected to upsampling; and
a display unit that displays an image reconstructed by the reconstruction calculating unit.

2. The X-ray CT apparatus according to claim 1,
wherein the upsampled-projection-data generating unit inserts a virtual channel in a view of the projection data, generates a virtual-counter-data space by applying a value of the virtual channel as a value of a corresponding point in a virtual view on the counter data, and calculates values of channels in the virtual view by using the values of the corresponding points and generates upsampled projection data in the view direction.

3. The X-ray CT apparatus according to claim 1,
wherein the upsampled-projection-data generating unit inserts a virtual channel in a view of the acquired projection data,
generates a virtual-counter-data space by applying the value of the virtual channel as a value of a corresponding point in a virtual view on the counter data, and calculates values of channels in the virtual view by using the values of the corresponding points on the virtual-counter-data space and generates upsampled projection data in a view direction and a channel direction.

4. The X-ray CT apparatus according to claim 1,
wherein the upsampled-projection-data generating unit inserts a virtual channel in a view of the acquired projection data,
generates a virtual-counter-data space by applying the value of the virtual channel as a value of a corresponding point in a virtual view on the counter data, calculates values of channels in the virtual view by using the values of the corresponding points and generates upsampled projection data in a view direction, a channel direction, and a slice direction.

5. The X-ray CT apparatus according to claim 2,
wherein upsampling on projection data is performed by the upsampled-projection-data generating unit in a case where an inter-view distance is larger than an inter-channel distance.

6. The X-ray CT apparatus according to claim 1,
wherein the upsampled-projection-data generating unit performs interpolation calculation using a weight coefficient that is obtained by using an inter-view distance and an inter-channel distance, thereby upsampling the projection data.

7. An X-ray CT apparatus comprising:
an X-ray tube device that performs irradiation with X-rays from a plurality of focus positions;
an X-ray detector that is disposed to face the X-ray tube device and detects transmitted X-rays as X-rays transmitted through an object;
a rotary disk on which the X-ray tube device and the X-ray detector are mounted and which rotates around the object;
a scanner gantry on which the rotary disk is mounted;
a couch on which the object is positioned;
a focus-shifted-scanning control unit that causes the couch and the scanner gantry to relatively move in a body-axial direction while causing the rotary disk to rotate and collects data of the transmitted X-rays from the X-rays with which irradiation is performed by causing the focus position to shift to any positions;

a projection-data converting unit that performs predetermined data processing on the collected data of transmitted X-rays from the focus positions and generates projection data required for reconstruction of a tomogram at a target slice position;

an upsampled-projection-data generating unit that generates virtual counter data containing counter data acquired on substantially coincident X-ray transmission path in the projection data, generates a virtual view in a view direction, and combines items of projection data of focus positions in which the virtual view is inserted, thereby generating upsampled projection data;

a reconstruction calculating unit that reconstructs an image by using the upsampled projection data; and a display unit that displays an image reconstructed by the reconstruction calculating unit.

8. The X-ray CT apparatus according to claim 7, further comprising:

a focus-shifted-projection-data generating unit that generates focus-shifted projection data acquired by combining items of the projection data at the focus positions without the virtual view inserted, wherein the image-reconstruction calculating unit reconstructs an image by using the focus-shifted projection data in a central region close to the center of the image from a predetermined boundary in an image plane, and by using the upsampled projection data in a peripheral region on an outer side from the boundary.

9. The X-ray CT apparatus according to claim 7, further comprising:

a focus-shifted-projection-data generating unit that generates focus-shifted projection data acquired by combining items of the projection data at the focus positions without the virtual view inserted, wherein the reconstruction calculating unit generates an image in which the focus-shifted projection data and the upsampled projection data are weighted and added in a predetermined ratio.

10. The X-ray CT apparatus according to claim 9, wherein the reconstruction calculating unit sets a weight coefficient that is used in the weighted addition such that spatial resolution of the image is smoothly continuous in a boundary region including a predetermined boundary in an image plane.

11. The X-ray CT apparatus according to claim 9, wherein the reconstruction calculating unit sets a range in which a weight coefficient that is used in the weighted addition changes such that predetermined spatial resolution is obtained at a predetermined position.

12. The X-ray CT apparatus according to claim 7, further comprising:

a focus-shifted-projection-data generating unit that generates focus-shifted projection data acquired by combining items of the projection data at the focus positions without the virtual view inserted; and a region-of-interest setting unit that sets a region of interest, wherein the reconstruction calculating unit further uses the focus-shifted projection data in the region of interest set by the region-of-interest setting unit.

13. The X-ray CT apparatus according to claim 7, wherein the upsampled-projection-data generating unit generates upsampled projection data that is different in the number of views, and wherein the reconstruction calculating unit generates an image obtained by using the upsampled projection data that is different in the number of views depending on a distance from the center of the image in the image plane.

14. The X-ray CT apparatus according to claim 7, wherein the upsampled-projection-data generating unit generates focus-shifted projection data acquired by combining, alternately in the view direction, first focus-shifted projection data obtained by causing the focus position to move in a positive direction of a channel direction of the X-ray detector and second focus-shifted projection data obtained by causing the focus position to move in a negative direction, and performs upsampling on the focus-shifted projection data in the view direction, thereby generating the upsampled projection data.

15. The X-ray CT apparatus according to claim 7, wherein the upsampled-projection-data generating unit performs upsampling, in the view direction, on first focus-shifted projection data obtained by causing the focus position to move in a positive direction of a channel direction of the X-ray detector and second focus-shifted projection data obtained by causing the focus position to move in a negative direction, and combines the upsampled first and second focus-shifted projection data alternately in the view direction, thereby generating the upsampled projection data.

16. The X-ray CT apparatus according to claim 14, wherein the upsampled-projection-data generating unit generates the upsampled projection data by further performing missing data processing on the projection data acquired by combining the upsampled first and second focus-shifted projection data alternately in the view direction.

17. The X-ray CT apparatus according to claim 14, wherein the upsampled-projection-data generating unit generates the upsampled projection data by further performing the upsampling in the view direction on the projection data acquired by combining the upsampled first and second focus-shifted projection data alternately in the view direction.

18. An upsampling method of projection data that is executed by an image calculating device, the method comprising:

a step of collecting data of object-transmitted X-rays measured by scanning of causing a couch and a scanner gantry to relatively move in a body-axial direction while causing a rotary disk of an X-ray CT apparatus to rotate;

a step of performing predetermined data processing on the collected data of object-transmitted X-rays and generating projection data required for reconstruction of a tomogram at a target slice position; and a step of generating virtual counter data containing counter data acquired on substantially coincident X-ray transmission path in the projection data, and upsampling the projection data.

* * * * *